US012605261B2

(12) United States Patent
Pulver et al.

(10) Patent No.: US 12,605,261 B2
(45) Date of Patent: *Apr. 21, 2026

(54) PROSTHETIC THUMB DEVICE

(71) Applicant: Point Designs, Inc., Broomfield, CO (US)

(72) Inventors: Ben Pulver, Lakewood, CO (US); Serena Kishek, Lakewood, CO (US); Levin Sliker, Boulder, CO (US); Stephen Huddle, Thornton, CO (US); Richard Weir, Lafayette, CO (US); Jacob Segil, Boulder, CO (US)

(73) Assignee: POINT DESIGNS, INC, Broomfield, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/673,232

(22) Filed: May 23, 2024

(65) Prior Publication Data

US 2024/0307196 A1 Sep. 19, 2024

Related U.S. Application Data

(63) Continuation of application No. 17/667,850, filed on Feb. 9, 2022, now Pat. No. 12,011,376.

(Continued)

(51) Int. Cl.
*A61F 2/58* (2006.01)
*A61F 2/80* (2006.01)
*A61F 2/78* (2006.01)

(52) U.S. Cl.
CPC .......... *A61F 2/80* (2013.01); *A61F 2002/587* (2013.01); *A61F 2002/7875* (2013.01)

(58) Field of Classification Search
CPC ........................... A61F 2002/587; A61F 2/586
See application file for complete search history.

(56) References Cited

U.S. PATENT DOCUMENTS 2,568,299 A * 9/1951 Philpott .................. A61F 2/586
623/64
2,669,727 A 2/1954 Opuszenski
(Continued)

FOREIGN PATENT DOCUMENTS

EP 2653137 10/2013
EP 2542189 5/2015
WO WO 2019/0324778 2/2019

OTHER PUBLICATIONS

Naked Prosthetics, "Home," https://www.npdevices.com, 10 pages, Nov. 15, 2019.
(Continued)

*Primary Examiner* — Bruce E Snow
(74) *Attorney, Agent, or Firm* — Brownstein Hyatt Farber Schreck, LLP

(57) ABSTRACT

Embodiments include a prosthetic thumb device that includes a track configured to attach to a prosthetic socket, a carriage, and a locking mechanism. The carriage can include a first component that couples to the track such that the carriage is operable to move along the track, and a second component that is configured to couple with a prosthetic digit and operable to rotate with respect to the first component. The locking mechanism can be coupled to the carriage and configured such that, in a first state, it prevents the carriage from moving along the track in a first direction and, in a second state, it allows the carriage to move along the track in the first direction. Embodiments can also include the track having a curved profile, and the carriage is operable to move along the curved profile of the track.

18 Claims, 21 Drawing Sheets

Related U.S. Application Data

(60) Provisional application No. 63/148,049, filed on Feb. 10, 2021.

(56) References Cited

U.S. PATENT DOCUMENTS

| | | | |
|---|---|---|---|
| 4,090,264 | A | 5/1978 | Thompson |
| 4,685,929 | A | 8/1987 | Monestier |
| 5,062,855 | A | 11/1991 | Rincoe |
| 5,219,366 | A | 6/1993 | Scribner |
| 6,908,489 | B2 | 6/2005 | Didrick |
| 8,100,986 | B2 | 1/2012 | Puchhammer et al. |
| 8,177,856 | B2 | 5/2012 | Jaworski |
| 9,072,614 | B2 | 7/2015 | Starkey et al. |
| 9,126,342 | B2 | 9/2015 | Birglen |
| 9,211,200 | B2 | 12/2015 | Moyer et al. |
| 9,370,430 | B2 | 6/2016 | Macduff |
| 9,375,319 | B2 | 6/2016 | Macduff |
| 9,629,371 | B2 | 4/2017 | Thompson, Jr. et al. |
| 9,707,101 | B2 | 7/2017 | Thompson, Jr. |
| 9,999,521 | B2 | 6/2018 | Thompson, Jr. et al. |
| 10,905,570 | B2 | 2/2021 | Segil et al. |
| 11,141,292 | B1 | 10/2021 | Dubre |
| 11,229,533 | B2 | 1/2022 | Segil et al. |
| 11,229,534 | B2 * | 1/2022 | Cabibihan ............... A61F 2/588 |
| 11,311,393 | B2 * | 4/2022 | Sampson ................. A61F 2/78 |
| 12,011,376 | B2 * | 6/2024 | Pulver .................... A61F 2/586 |
| 2005/0043822 | A1 | 2/2005 | Didrick |
| 2006/0212129 | A1 | 9/2006 | Lake |
| 2010/0036507 | A1 | 2/2010 | Gow |
| 2012/0146352 | A1 | 6/2012 | Haslinger |
| 2012/0330432 | A1 | 12/2012 | Fong |
| 2013/0046395 | A1 | 2/2013 | McLeary |
| 2014/0303741 | A1 | 10/2014 | Macduff |
| 2015/0374515 | A1 | 12/2015 | Meijer et al. |
| 2016/0089251 | A1 | 3/2016 | Mandl |
| 2017/0049583 | A1 | 2/2017 | Belter |
| 2019/0183661 | A1 | 6/2019 | Gill et al. |
| 2019/0298553 | A1 | 10/2019 | Gibbard et al. |
| 2019/0328550 | A1 | 10/2019 | Akhtar |
| 2020/0022824 | A1 * | 1/2020 | Evans ........................ A61F 2/70 |
| 2020/0155330 | A1 * | 5/2020 | Segil ......................... A61F 2/72 |
| 2021/0177627 | A1 | 6/2021 | Segil et al. |
| 2022/0133509 | A1 | 5/2022 | Segil et al. |
| 2022/0346985 | A1 | 11/2022 | Pulver |

OTHER PUBLICATIONS

Partial Hand Solutions LLC, "Prosthetic Devices," https://partialhandsolutions.com, 6 pages, Nov. 15, 2019.

Point Designs LLC, "The Point Digit II," 9 pages, Nov. 18, 2019.

Segil et al., "The Point Digit: Mechanical Design and Testing of a Ratcheting Prosthetic Finger," 41st Annual Meeting of the American Society of Biomechanics, 2 pages, Aug. 8-11, 2017.

Ten Kate, et al., "3D-Printed Upper Limb Prostheses: A Review," Disability and Rehabilitation: Assistive Technology, vol. 12, No. 3, pp. 300-314, Feb. 2, 2017.

Touch Bionics, "i-limb digits Clinician Manual," Issue No. 2, 38 pages, Dec. 2014.

Extended European Search Report issued Nov. 8, 2024 in corresponding European application No. 24177919.8.

* cited by examiner

800

802

900

902

PROSTHETIC THUMB DEVICE

CROSS-REFERENCE TO RELATED APPLICATION

This application is a continuation patent application of U.S. patent application Ser. No. 17/667,850, filed Feb. 9, 2022, and titled "PROSTHETIC THUMB DEVICE", which claims the benefit of U.S. Provisional Patent Application No. 63/148,049, filed Feb. 10, 2021, the contents of which are incorporated herein by reference in their entirety.

FIELD

The described embodiments relate generally to prosthetic devices. More particularly, the present embodiments relate to prosthetic devices for the hand.

BACKGROUND

Finger or partial hand prostheses can be used to restore function and/or appearance of a missing finger or thumb. The thumb is particularly important to hand function as it is used in almost all types of gripping. The thumb also significantly contributes to grip strength. Much of the thumb's importance in normal hand function comes from the greater range of movement of the thumb compared to other fingers and the thumb's position relative to the other fingers. Accordingly, thumb amputation can cause a significant loss of hand functionality.

Traditional thumb prostheses position the prosthesis in a fixed location with respect to other fingers of the hand. In this regard, these types of prostheses can have significantly limited ranges of motion as compared to the natural thumb. A user may desire a prosthetic device that provides a greater range of motion that is typical of a natural thumb.

SUMMARY

Embodiments described herein are directed to a prosthetic thumb device that includes a track configured to attach to a prosthetic socket and a carriage. The carriage can include a first component that couples to the track such that the carriage is operable to move along the track, and a second component that is configured to couple with a prosthetic digit and is operable to rotate with respect to the first component. The prosthetic thumb device can also include a locking mechanism coupled to the carriage and configured to, while in a first state, prevent the carriage from moving along the track in a first direction and, while in a second state, allow the carriage to move along the track in the first direction.

Embodiments described herein are also directed to a thumb prosthesis that includes a track defining a curved profile and operable to connect to a prosthetic socket, and a slider that couples to the track and is configured to move along the curved profile of the track. The thumb prosthesis can also include a top component that is attached to the slider and is operable to couple with a prosthetic digit, and a locking mechanism coupled to the slider and operable to transition between a first state that prevents movement of the slider along the track and a second state that allows the slider to move along the track.

Embodiments described herein also include a prosthetic device that includes a track defining a curved profile that is configured to extend between a first region of a prosthetic socket that corresponds to a region of a hand that is between a thumb and an index finger, a second region of the prosthetic socket that corresponds to a palm region of the hand, and a carriage configured to couple to the track, move along the curved profile, and couple to a prosthetic.

BRIEF DESCRIPTION OF THE DRAWINGS

The disclosure will be readily understood by the following detailed description in conjunction with the accompanying drawings, wherein like reference numerals designate like structural elements, and in which.

Figure 1:
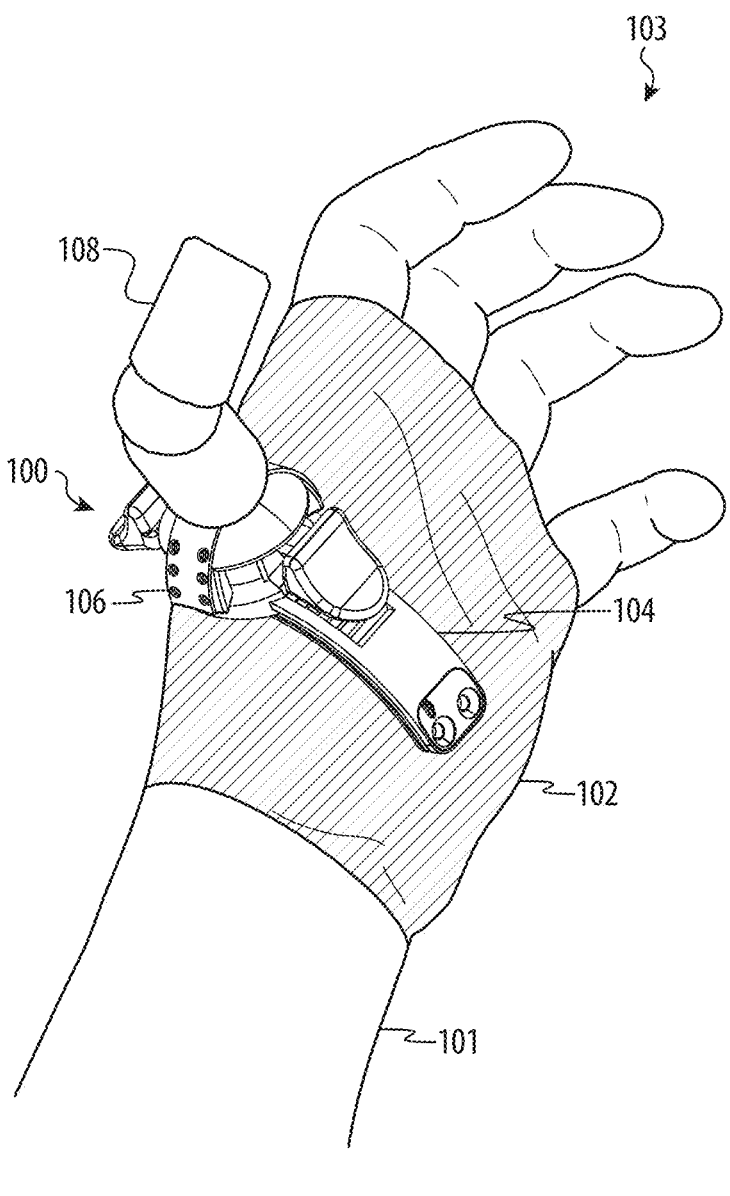
FIG. 1 shows an example prosthetic device attached to a hand of a user.

It should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

Embodiments described herein are directed to a prosthetic device that helps restore functions of a user's hand that were performed by a lost digit such as a thumb. The prosthetic device can allow a user to move their prosthetic digit, such as a thumb, in adduction and/or abduction-type motions to position and secure the prosthetic digit in a variety of different orientations relative to other digits on their hand. For example, when the user is not using their hand for any specific task, they may position the prosthetic digit in a typical resting position such as a flat or open hand orientation. When the user wants to perform a specific task, they can position the prosthetic digit in a desired orientation relative to the other fingers. For example, to grip an object, a user can move the prosthetic digit into an opposed orientation relative to their other fingers. The prosthetic device described herein can allow a user to position their prosthetic digit in a variety of different orientations relative to their other digits to help restore normal functioning of the user's hand.

When a person loses a digit such as a thumb, a prosthetist typically creates a prosthetic socket that interfaces with the remaining portion of the person's hand. One or more prosthetic digits can be coupled to the remaining portion of the hand using the prosthetic socket. Prosthetic sockets are typically custom made by a prosthetist to suit the needs of each person. The prosthetic devices described herein can be coupled to a prosthetic socket to secure a prosthetic digit such as a prosthetic thumb to the user's hand. For clarity and the sake of illustration, the prosthetic device is described in relation to a prosthetic thumb. However, the prosthetic device and/or features of the prosthetic devices described herein can be used with or in place of other digits of the hand. Additionally, the concepts relating to the prosthetic device can be applied to other joints, such as a shoulder or elbow. For example, the prosthetic device can be applied to a prosthetic elbow socket to attach a lower arm prosthesis to a user's upper arm. In the example of an elbow, the prosthetic device can allow the user to positon and secure their lower arm prosthesis in a variety of different orientations to help restore normal function of a lost elbow joint.

The prosthetic device typically includes a track that couples to a prosthetic socket. The track can extend over the thumb region of a user (e.g., the portion of the hand where the thumb is or was located) and at least partially across the palm of the user's hand. The prosthetic device can also include a carriage that moves along the track and movably couples a prosthetic digit, such as a prosthetic thumb, to the track. Accordingly, the carriage can be used to move the prosthetic digit across a portion of the user's hand to achieve ranges of motion for the prosthetic digit that are typical of a natural thumb. The prosthetic device can move a prosthetic digit abductively and/or adductionally to position the prosthetic digit in a variety of orientations with respect to the other fingers of the hand. For example, the prosthetic device can be used by a user to position a prosthetic digit in and out of opposition with other fingers of the user's hand. As used herein, the term "opposition" is used to describe movement of a prosthetic thumb (or natural thumb) that brings the prosthetic thumb into contact with the one or more fingers of the hand. For example, opposition includes motion that brings the tip of a prosthetic thumb in contact with the tip(s) of one or more other digits of the hand.

The prosthetic device can include a locking mechanism that secures the carriage in a specific orientation relative to the track. For example, the user can move the carriage along the track to position their prosthetic digit in a desired orientation, and then engage the locking mechanism to prevent the carriage and the prosthetic thumb from moving along the track. Accordingly, the user can position their prosthetic digit for a specific task and the thumb can remain securely locked while they perform that task. In some cases, the locking mechanism can be manually engaged and/or disengaged by the user, such that, each time the user wants to move their prosthetic digit, they disengage the locking mechanism. The user then reengages the locking mechanism to lock the prosthetic digit in position.

In other cases, the locking mechanism may automatically default to a certain state, such as a locked state, and a user may engage a release feature of the locking mechanism to move the carriage. For example, when the user is not engaging the release feature, the locking mechanism can engage with the track to prevent the carriage from moving relative to the track. In such cases, to move their prosthetic digit, the user engages the release feature, which allows the carriage and prosthetic digit to move along the track. When the user disengages the release feature, the locking mechanism can automatically reengage with the track to lock the carriage, and thus the prosthetic digit, in position. Accordingly, the user need only engage the locking mechanism and position the prosthesis, which is then automatically secured in its new position. The automatic re-locking of the carriage to the track simplifies positioning a prosthetic digit, or other prosthesis.

In certain embodiments, the locking mechanism can transition between different states, which may include any or all of: a free movement state in which the carriage can move in either direction along the track; a semi-free state in which the carriage can freely move in at least one direction while the locking mechanism prevents it from moving in at least one other direction; and a locked state in which the carriage does not move in any direction without user input. Each of these states, along with other embodiments, are described herein.

In other cases, the locking mechanism can orient the release feature such that a direction of force required to disengage the locking mechanism is similar or substantially the same as the direction of force that causes the carriage to move along the track. In this regard, the user can disengage and move the carriage using the same or similar point of contact. This may help a user easily position their prosthetic digit using body parts or other objects around them, which keeps the user's other hand free to perform other tasks. For example, a user may be able to unlock and move the prosthetic digit by pressing the engagement feature against their side or objects around them.

The carriage can be implemented in a variety of ways. In some cases, the carriage includes a first component that couples to the track and a second component that couples to a prosthetic digit. For example, the first component can be a sliding component that slides along the track to move the prosthetic digit to different orientations relative to the hand.

The second component can have one or more features for coupling to a prosthetic digit. For example, the second component could include threaded holes that can be used to mechanically fasten the prosthetic digit to the second component. In other cases, the second component and the prosthetic digit can be coupled using other mechanical fastening mechanisms such as snap features, tabs, interference fits, and so on; welding; adhesives; or any other suitable fastening mechanism, or combinations thereof. The first and second components can also couple to each other in a variety of ways including using mechanical fastening techniques, welding, adhesives, and so on, or combinations thereof. In some embodiments, the second component can move relative to the first component such that an orientation of the prosthetic digit relative to the track can be adjusted. For example, the second component can be configured to rotate relative to the first component such that an angular orientation of the prosthetic digit relative to the track can be changed. In other cases, the first and second components can be formed from a single piece of material. In yet other embodiments, the prosthetic digit can be configured to mount in different orientations relative to the carriage such that the orientation of the prosthetic digit relative to the track and/or hand can be adjusted based on how the orientation of that prosthetic digit is mounted to the carriage.

These and other embodiments are discussed below with reference to FIGS. 1-19B. However, those skilled in the art will readily appreciate that the detailed description given herein with respect to these Figures is for explanatory purposes only and should not be construed as limiting.

FIG. 1 shows an example of a prosthetic device 100 attached to a prosthetic socket 102 that is being worn by a user 101. The prosthetic device 100 can include a track 104 that attaches to the prosthetic socket 102 and a carriage 106. Generally, the carriage 106 is attached to, and can move along, the track 104. A prosthetic digit 108 can be attached to the carriage 106. The prosthetic device 100 allows a user 101 to position their prosthetic digit 108 in a variety of different orientations by moving the carriage 106 along the track 104. Movement of the carriage 106 along the track 104 can help to restore movement that is typical of a natural thumb such as the abduction and adduction motions that move a thumb into and out of opposition with the other digits 103.

The track 104 can mount to the prosthetic socket 102 in a variety of ways. In some cases, the track 104 can be coupled to the prosthetic socket 102 using one or more mechanical fasteners such as screws, bolts, rivets, pins or any other suitable fastener. In some embodiments, an anchoring mechanism can be formed on the prosthetic socket 102, and the track 104 can be fastened to the anchoring mechanism. For example, the anchoring mechanism could be a plate that is contained within the bulk of the prosthetic socket 102. For example, the anchoring mechanism can be laminated between different layers of the prosthetic socket 102 when the prosthetic socket 102 is being built. The track 104 can be coupled to the prosthetic socket 102 using the anchoring mechanism such as by bolting the track 104 to the anchoring mechanism. In some embodiments, the track can be coupled to the prosthetic device using adhesives, by welding the track to the prosthetic socket or one or more parts attached to the prosthetic socket, through interference fit features, or using any other suitable attachment means or combinations of different attachment methods.

The range of motion of the prosthetic digit 108 generally depends on the orientation of the track 104 with respect to the prosthetic socket 102, which is typically set when the track is mounted to the prosthetic socket 102. In some embodiments, the track 104 may be mounted to the prosthetic socket 102, but may be repositionable therein, for example by rotating or shifting the track with respect to the socket, or the like. In this regard, the track 104 can be shaped to impart a desired range of motion to the prosthetic digit 108. In some cases, the track 104 can have a constant radius of curvature such that the carriage 106 and the prosthetic digit 108 move along the track 104 in a circumferential path. For example, a length of the track 104 can be curved, and, when the track 104 is attached to the prosthetic socket 102, the curve of the track 104 extends from a thumb region to a palm region of the prosthetic socket 102. As the carriage 106 and the prosthetic digit 108 move along the curve of the track 104, the center of motion of the carriage 106 can be located at the axis of the curvature of the track 104. In some embodiments, the combination of the curvature of the track 104 and the positioning of the track 104 on the prosthetic socket 102 can locate the center of motion within the hand or at a position that is remote from the mounting location of the track 104. Such configurations can result in an externally mounted device such as the prosthetic device 100 being able to impart similar motion to the prosthetic digit 108 as an internal joint does to a natural thumb. In this regard, the shape of the track 104 and its orientation on the prosthetic socket 102 can be configured such that the movement of the prosthetic digit 108 can achieve similar motion to the motion of a natural thumb.

In other embodiments, the shape of the track 104 can conform to the shape of the prosthetic socket 102, whether as initially made or when mounted to the socket. For example, the track 104 can be formed in an initial shape such as a planar or curved structure, and can be deformed to adapt to the shape of the prosthetic socket 102. In yet other examples, the track 104 can be curved along multiple dimensions such that as the carriage is moved along the track it can both translate and rotate the prosthetic digit 108 in multiple axes, which may help the prosthetic digit 108 replicate the motion of a natural thumb. In yet other embodiments, the track 104 can be planar and be mounted to a relatively flat portion of the prosthetic socket 102, such as a palm region of the prosthetic socket 102.

Figure 2A:
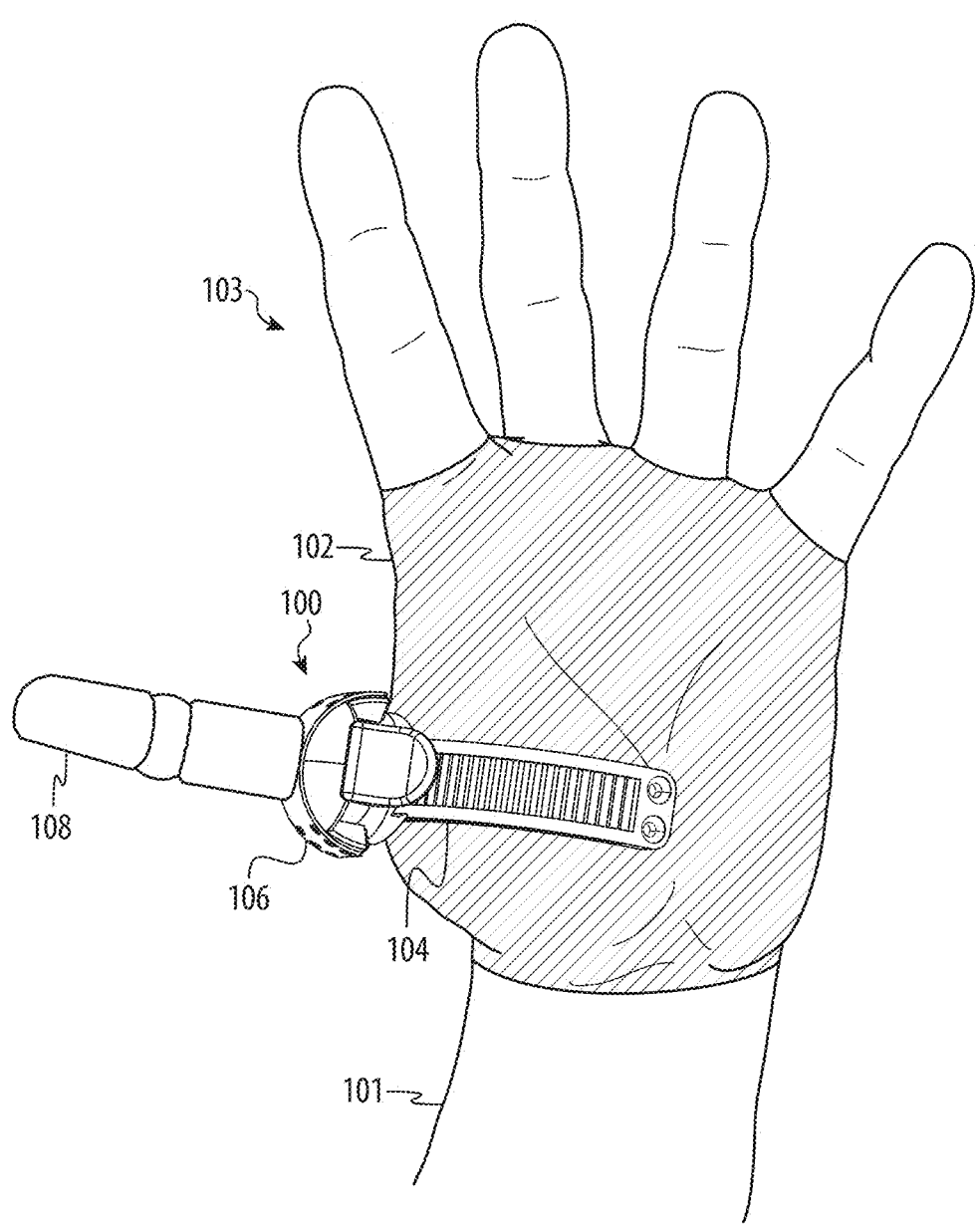
FIG. 2A shows the example prosthetic device of FIG. 1 in a first position and attached to a wearer's hand.
Figure 2B:
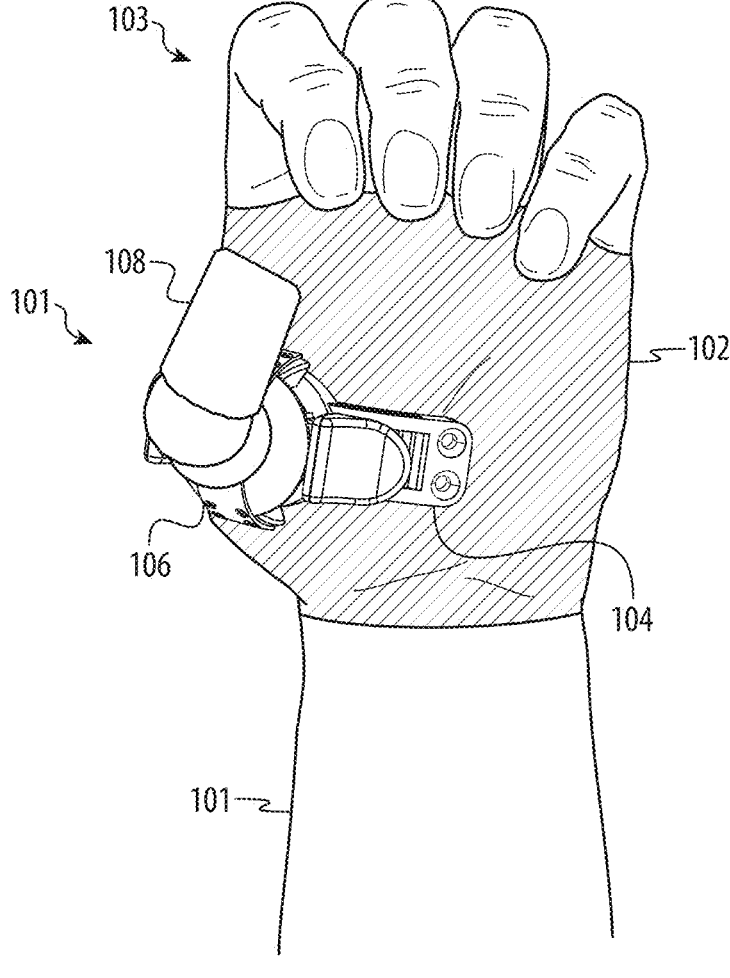
FIG. 2B shows the example prosthetic device of FIGS. 1 and 2A in a second position and attached to a wearer's hand.

FIG. 2A shows an example of the prosthetic device 100 with the carriage 106 located at a first position along the track 104; FIG. 2B shows an example of the carriage 106 located at a second position along the track 104. As described herein, the carriage 106 can move along the track 104 to position the prosthetic digit 108 in different orientations relative to the other digits 103 of the hand. As shown in FIG. 2A, the carriage 106 can be positioned at a first region of the prosthetic socket 102 that corresponds to a region of that hand that is between the thumb and index finger. In this position, the carriage 106 can position the prosthetic digit 108 such that the prosthetic digit 108 can be situated in a flat orientation relative to the other digits 103 of the hand. As used herein the term "flat orientation" refers to an orientation in which the thumb is adducted such that it is positioned in relatively the same plane as the other digits 103 and/or the palm as shown in FIG. 2A, or in a plane that is substantially parallel to the plane of the other digits. The term "flat orientation" is meant to encompass the orientations of the thumb relative to the other digits 103 that are typical of a resting position for the hand or natural variations that are typical of a resting hand position.

As shown in FIG. 2B, the carriage 106 can be moved along the track 104 and positioned at a second region of the prosthetic socket 102 within, or corresponding to, a palm region of a hand. In this position, the carriage 106 can position the prosthetic digit 108 such that the prosthetic digit 108 can be situated in an opposed orientation with at least one of the other digits 103. As used herein, the term "opposed orientation" refers to an orientation in which at least a portion of the thumb (typically a distal/end portion) is positioned opposite one of the other digits 103 as shown in FIG. 2B. The opposed orientation is meant to encompass the orientations of the thumb relative to the other digits 103 that are typically used while gripping objects or performing other tasks in which the thumb opposes forces generated by the fingers and/or other portions of the hand such as the palm.

FIGS. 2A and 2B show two example positions of the carriage 106 relative to the track 104 and the prosthetic socket 102. In some embodiments, the carriage 106 can be moved to any position along the track 104, and thus can be positioned by a user 101 in a wide range of different positions relative to the prosthetic socket 102 and the other digits 103. In some cases, a length, shape, and mounting location of the track 104 on the prosthetic socket 102 can be configured to facilitate specific positions and/or movement of the prosthetic digit 108 with respect to the other digits 103. For example, the track 104 can be configured such that the carriage 106 is operable to be positioned at different locations along the track 104 that allow the prosthetic digit 108 to be placed in opposition with each of the other digits 103. In other cases, the track 104 can be configured to impart motion on the prosthetic digit 108 that is greater than the movement that is achievable by a natural thumb. For example, the track 104 can be configured to wrap around a back portion of a user's hand thereby allowing the carriage 106 to impart a greater range of motion to the prosthetic digit 108 as compared to a natural thumb.

Figure 3A:
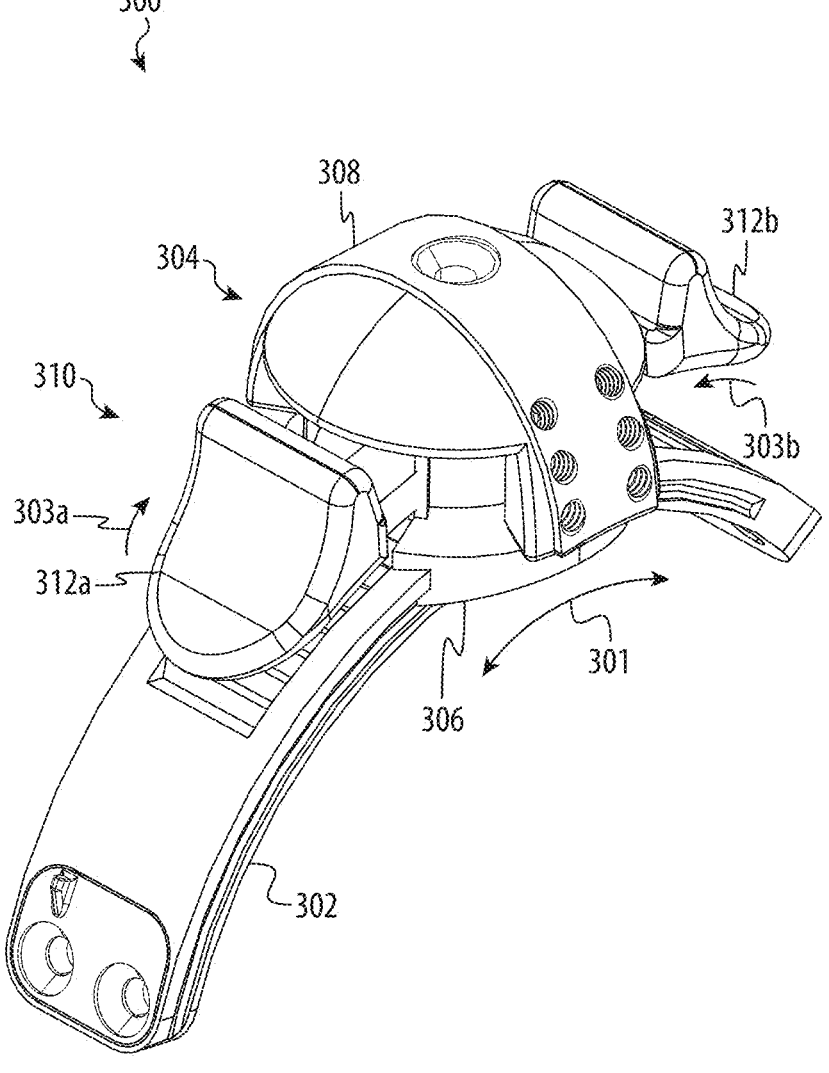
FIG. 3A shows an example prosthetic device.

FIG. 3A shows an example of a prosthetic device 300, which can be an example of the prosthetic devices described herein such as prosthetic device 100 described with reference to FIGS. 1 and 2A-2B. The prosthetic device 300 can include a track 302, which can be an example of the tracks described herein such as track 104; a carriage 304, which can be an example of the carriages described herein such as carriage 106; and a locking mechanism 310. In some embodiments, the carriage 304 can include a first component 306 that attaches to the track 302, and a second component 308 that attaches to a prosthetic digit, such as a prosthetic thumb as descried herein.

The first component 306 of the carriage 304 can attach to the track 302 to enable the carriage to move back and forth along a length 301 of the track 302. In cases where the track 302 is curved, the first component 306 can be configured to traverse the curved profile of the track 302. The first component 306 can be a component that slides along the track 302, and may be referred to as a slider. In some cases, the first component 306 can include bearings, rollers, or other rotatable structures that engage with the track 302 to move the first component 306 along the track. Additionally or alternatively, the track 302 can include one or more bearings, rollers, or other rotatable structures that interface with the first component 306 to facilitate movement of the first component 306 along the track.

The second component 308 can attach to the first component 306 and also attach to a prosthetic digit, such as the prosthetic digits described herein. In some cases, the second component 308 can be removably coupled to the first component 306, for example, by using one or more mechanical fasteners, such as bolts, screws, rivets, interface fit connections, or other suitable fastening techniques. In this regard, the second component 308 can be separated from and reconnected to the first component 306. In other cases, the second component 308 can be coupled to the first component 306 by welding, adhesives, or other suitable permanent or semi-permanent attachment technique. In yet further cases, the second component 308 and the first component 306 can be formed from a single piece of material through processes such as machining, molding, additive manufacturing, or other suitable techniques.

The locking mechanism 310 can interface with the track 302 and the carriage 304, and secure the carriage 304 in a fixed position relative to the track 302. In some cases, the locking mechanism 310 can be at least partially contained within the carriage 304. For example, the locking mechanism 310 can include one or more actuators 312 that have parts, which are positioned within a recess formed in the carriage 304. The actuators 312 can engage and/or disengage the locking mechanism 310 to allow or prevent movement of the carriage 304 along the track 302.

In some cases, engagement of one or more of the actuators 312 can transition the locking mechanism 310 from a locked state to an unlocked state. For example, in the locked state, the locking mechanism 310 prevents movement of the carriage 304 along the track 302. A user can switch the locking mechanism 310 to an unlocked state by engaging one or more of the actuators 312, and, in the second state, the user can move the carriage 304 along the track 302. In these cases, the locking mechanism 310 may switch between the locked state and the unlocked state, and remain in the state that was last engaged by the user. For example, if the user engages an actuator(s) 312 to transition to the locked state, the locking mechanism 310 may remain in that locked state until the user reengages an actuator(s) 312 to transition the locking mechanism 310 to the second unlocked state. In this regard, one or more of the actuators 312 can be engaged once to unlock and a second time to lock, and vice versa. The mechanical functioning of the locking mechanism is further described throughout the application, for example in relation to FIGS. 10A-10C.

In some embodiments, the locking mechanism 310 can automatically default to a locked state. For example, in the absence of a user interaction, the locking mechanism 310 secures the carriage 304 to the track 302 to prevent movement of the carriage 304 along the track 302. In the locked state, the locking mechanism 310 can prevent movement of the carriage 304 along the track 302 in a single direction or both directions. In these cases, a user would need to engage and remain engaged with one or more of the actuators 312 to enter the unlocked state to move the carriage 304 along the track 302. Upon the user releasing the actuator(s) 312, the locking mechanism 310 can re-enter the locked state to prevent movement of the carriage 304 along the track 302. In other cases, the locking mechanism 310 can default to an unlocked state and the user may need to remain engaged with one or more of the actuators to enter the locked state.

In some cases, different actuators 312 can control movement of the carriage 304 in different directions along the track 302. For example, a first actuator 312a can control movement of the carriage 304 in a first direction 303a, and/or a second actuator 312b can control movement of the carriage 304 in a second direction 303b. Operation of the locking mechanism 310 is further described herein, for example in relation to FIGS. 10A, 10B, and 10C.

Figure 3B:
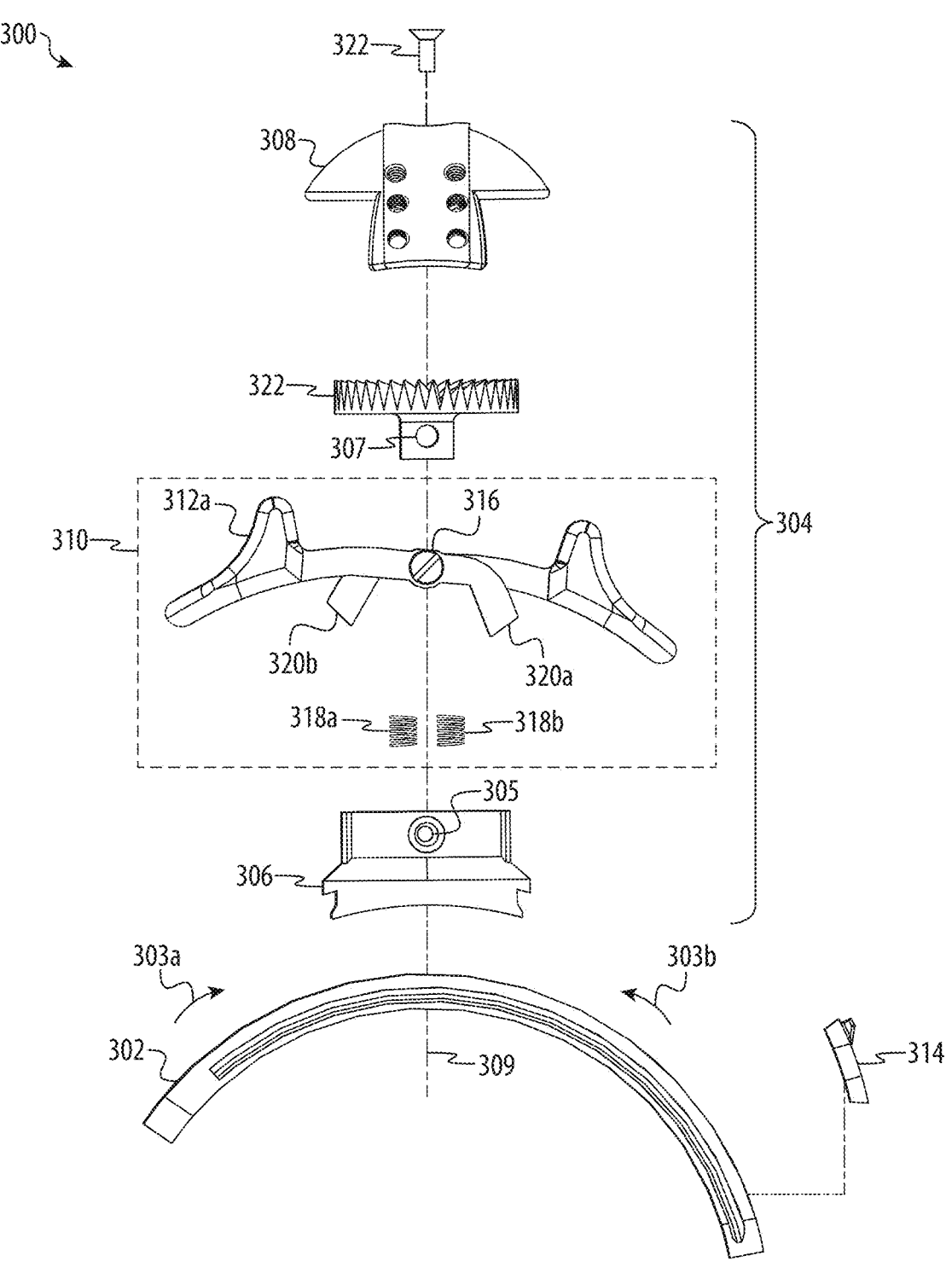
FIG. 3B shows an exploded view of the prosthetic device shown in FIG. 3A.

FIG. 3B shows an example of an exploded view of a prosthetic device 300. The prosthetic device 300 can further include a stopping mechanism 314 that attaches to the track 302. The stopping mechanism 314 can be removed to allow the first component 306 to decouple from the track 302. In this regard, after the track 302 is mounted to a prosthetic socket, the carriage 304 can be connected or removed from the track 302 by detaching the stopping mechanism 314 from the end of the track 302. In other cases, the stopping mechanism 314 can be integrated with the track 302. For example, the stopping mechanism 314 could be implemented as a spring mechanism, a sliding mechanism, or other suitable component that, when in a first position, prevents the carriage from detaching from the track 302, and when moved to a second state, allows the carriage 304 to detach from the track 302.

The prosthetic device 300 can also include a fastening feature 316, such as a pin, screw, or the like, that attaches at least part of the locking mechanism 310 to the carriage 304. For example, the fastening feature 316 can couple one or more actuators 312 to the first component 306 such that the actuator(s) 312 can pivot with respect to the first component 306. The pivoting motion of the actuators 312 can allow them to engage or disengage with the track 302 to transition between the locked and unlocked states.

In some embodiments, the locking mechanism 310 can include one or more biasing elements 318 which can bias the locking mechanism 310 into a default state such as the locked or unlocked default states as described herein. For example, a first biasing element 318a can include a spring that pushes up against the first actuator 312a causing the first actuator 312a to pivot about the fastening feature 316 thereby engaging the first end 320a with the track 302 to prevent movement of the carriage 304 along the track 302 in the first direction 303a. A second biasing element 318b can include a spring that pushes up against the second actuator 312b causing the second actuator 312b to pivot about the fastening feature 316 thereby engaging the second end 320b with the track 302 to prevent movement of the carriage 304 along the track 302 in the second direction 303b. In other cases, the first actuator 312a can prevent movement of the carriage 304 along the second direction 303b, and the second actuator 312b can prevent movement of the carriage 304 in the first direction 303a. In some cases, the locking mechanism 310 can include a single actuator 312 and engagement of that actuator 312 can prevent or permit movement in a single direction along the track 302 or both directions along the track 302.

Additionally or alternatively, the locking mechanism 310 can position bias elements (such as biasing elements 318) above the actuators. In this regard, the biasing elements can push down (or, in some embodiments, up or in another direction) on one or more of the actuators 312 to engage the ends 320 with the track 302. In other examples, the locking mechanism 310 can include torsion springs, cantilevered springs, or other configurations of biasing elements that are used to engage the ends 320 with the track 302. In yet other examples, the biasing elements can include elastically compressible or extendible materials such as an elastomer.

In some embodiments, the carriage 304 includes a rotational component 322 that couples the second component 308 to the first component 306. In some embodiments, the rotational component 322 can be coupled to the first component 306 by the fastening feature 316. For example, the fastening feature 316 can be a threaded fastening feature 316 and interface with both a threaded feature 305 on the first component 306 and a hole feature 307 on the rotational component 322 to couple both the actuator(s) 312 and the rotational component 322 to the first component 306. In other cases, the fastening feature 316 can be a pin, rod, or other suitable fastener, and the first component 306 and the second component 308 can include complementary fastening structures to interface or accept the fastening feature 316. The second component 308 can be coupled to the rotational component 322 using a second fastening feature 324 as described herein. The fastening feature 316 and the second fastening feature 324 can be the same type (e.g., threaded fasteners) or different types (e.g., the fastening feature 316 is a pin and the second fastening feature 324 is a threaded fastener).

The rotational component 322 can also be configured to position and/or secure the second component 308 at different axial orientations about axis 309 and with respect to the first component 306. In some cases, the rotational component 322 can include a first set of teeth and the second component 308 can include a second set of teeth that engages with the first set of teeth. In this regard, the second component can be rotated with respect to the first component 306 and secured to the rotational component 322 to allow a prosthetic digit to be positioned at different axial orientations relative to a prosthetic socket and other fingers of the hand.

In some embodiments, the second component 308 and the rotational component 322 can include a user lockable feature that allows a user to selectively rotate the second component 308 (and an attached prosthetic digit) about axis 309. In this regard, a user can engage the lockable feature to change the axial position of an attached prosthetic digit relative to the rest of the prosthetic device 300 and hand of the user. Such a lockable feature can allow additional adjustment of a prosthetic digit such as a prosthetic thumb relative to other digits of the hand. In some cases, the lockable feature can include a spring mechanism that holds the teeth of the second component 308 engaged with teeth of the rotational component 322. This spring mechanism can allow the user to separate (e.g., pull) the second component 308 away from the rotational component 322, thereby allowing the second component 308 to be rotated by the user. Upon release of the second component 308, the spring mechanism can cause the teeth of the second component 308 to re-engage with teeth of the rotational component 322 thereby locking the second component (and prosthetic digit) in a different axial orientation. In some cases, this lockable feature can include a pin or other device that is used to selectively allow rotation of the second component 308.

Figure 4:
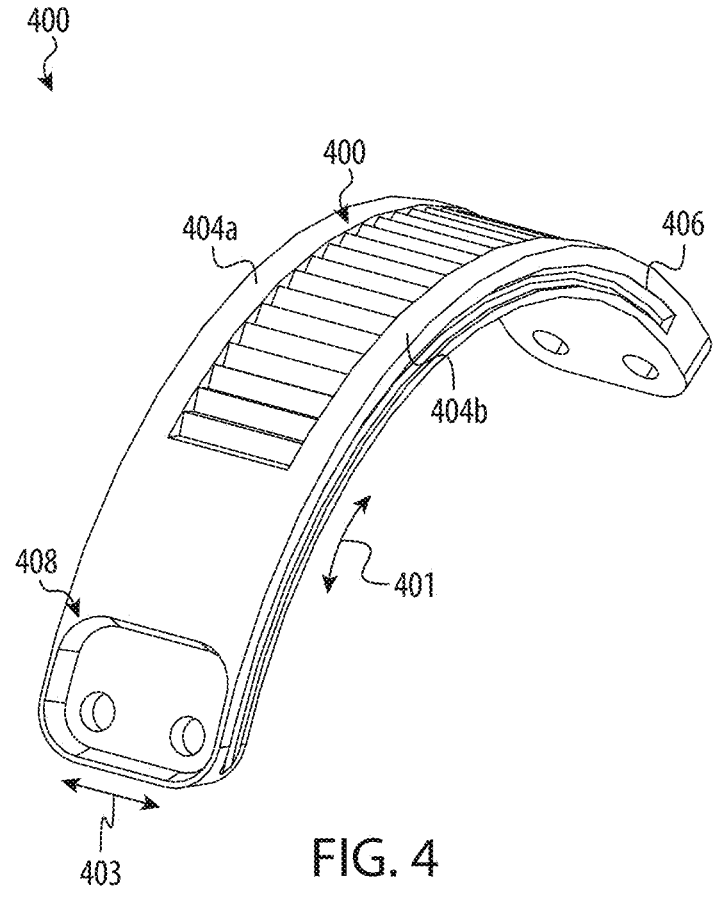
FIG. 4 shows an example track for a prosthetic device.

FIG. 4 shows a track 400, which can be any of the tracks discussed herein, such as tracks 104 and 302. In some embodiments, the track 400 can curve along its length 401. The curve of the track 400 can have a constant radius, or can have a variable radius/multiple radii. In some cases, the track 400 can have multiple curves along the length dimension 401, for example creating one or more peaks and valleys. In other cases, the track 400 curves along both the length dimension 401 and a width dimension 403. In yet other examples, the track 400 can further twist along the length 401. Such curving and twisting of the track 400 can be used to dynamically change an orientation of a prosthetic digit relative to other digits of the hand as it moves along track 400.

The track 400 can be made from materials such as metal, polymer, ceramics, or other suitable material, or combinations thereof. The track 400 can include a locking feature 402 that interacts with a locking mechanism to prevent movement of a carriage along the track as described herein. In some cases, the locking feature 402 can be a set of teeth that extends along a length dimension of the track 400. In other cases, the locking feature 402 could include holes, pins, ridges, or other features that can be engaged by the locking mechanism and prevent movement of the carriage along the track 400. In some cases, the locking feature can include different surface finishes on one or more surfaces of the track 400 and the locking mechanism can lock using frictional forces with the track 400.

In some cases, the track 400 can include one or more surfaces 404 across which a carriage can slide as it moves along the track 400. In some cases, these surfaces 404 can include surface finishing, different materials, coatings, or other features that facilitate sliding of the carriage along the track and/or reduce wear. For example, the surfaces 404 extending along the upper edges of the track 400 could include a coating that reduces friction, or be formed from a material that has higher resistance to wear such as ceramic as compared to a material that other portions of the track 400 are made from. In some cases, a first surface 404*a* may be positioned on a first side of the locking feature and a second surface 404*b* can be positioned on a second side of the locking feature 402; the first and second sides may be adjacent or opposing.

The track 400 can also include one or more retention features 406 that interface with a carriage to secure the carriage to the track 400. For example, the retention features 406 could include a channel extending along each side of the track 400. In some cases, these channel(s) can include one open end such that a carriage can be slid on and off that end of the track 400 and a closed end to prevent the track from sliding off the other end. In some cases, the channel(s) can be open at each end of the track 400.

The track 400 can also include one or more attachment interfaces 408, which can be used to secure the track 400 to a prosthetic socket as described herein. In some cases, the attachment interface can accept a plate that couples to the prosthetic socket. In other cases, the attachment interfaces 408 could include holes or other features that use fasteners such as bolts or screws to attach directly to the socket.

In some embodiments, the track 400 can include rails that are connected by one or more cross members. The rails could be flat, cylindrical, or other suitable shape, and the carriage could have a complementary interface feature. For example, the track can include cylindrical rails extending from a first end to a second end, and the carriage can have concave wheels that at least partially wrap around the cylindrical rails. In other cases, the track can be formed from a singular cylindrical rail or other rail structure having a curved cross-section.

Figure 5:
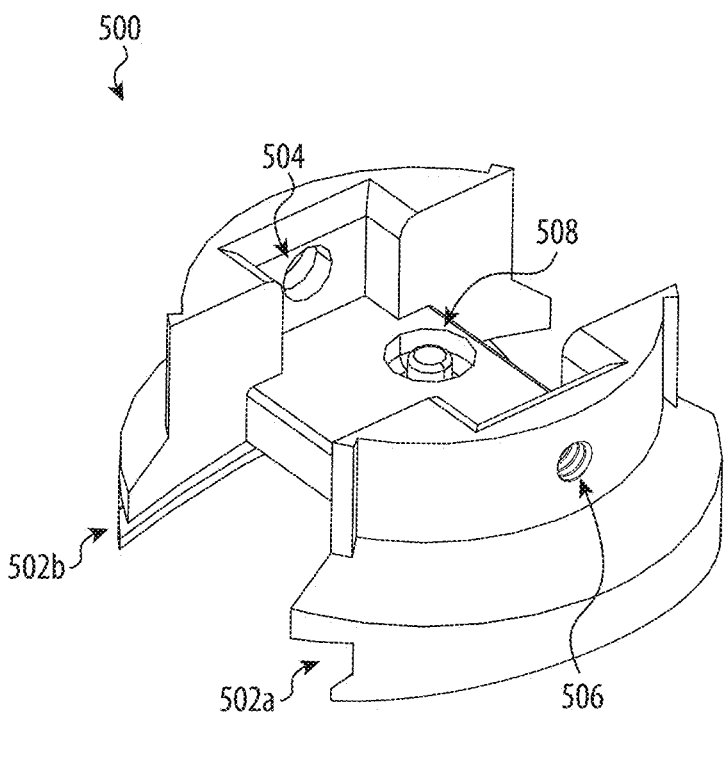
FIG. 5 shows an example slider component for a prosthetic device.

FIG. 5 shows an example first component 500 for a prosthetic device, which can be an example of the first component 306 described herein. In some cases, the first component 500 can be a component that slides along the track, and may be referred to as a slider. The first component 500 can include one or more rails 502 that engage with the track as described herein. The rails 502 can interface with the retention features 406 of the track such as the channels described with reference to FIG. 4. In some cases, the profile of the rails can match a profile of the track to facilitate movement of the first component 500 along the track. For example, if the track has a radius of curvature, the rails 502 can be configured to have substantially the same curvature. In further embodiments, the rails 502 could have a specific surface finish, coating, or include different materials, which can be used to reduce friction, increase wear resistance, or otherwise adjust how the first component 500 moves along the track. In yet further examples, the rails can include bearings, wheels, or other components that rotate as the first component 500 is moved along the track.

The first component 500 can include a fastening feature that includes an opening 504 and a thread feature 506 for accepting a mechanical fastener (such as a bolt) in order to attach to other components, such as the locking mechanism and the rotational component as described herein. In some embodiments, other fasteners could be used such as a pin/rod that is press fit, riveted, welded, adhesively coupled, or otherwise attached to the first component 500. The opening 504 may be defined in a recess within a sidewall of the first component 500, as shown.

In some embodiments, the first component 500 can include one or more seating features 508 for a biasing element such as the biasing element(s) 318 discussed in relation to FIG. 3B. The seating feature(s) 508 can help position and/or retain the biasing element in a desired orientation.

Figure 6:
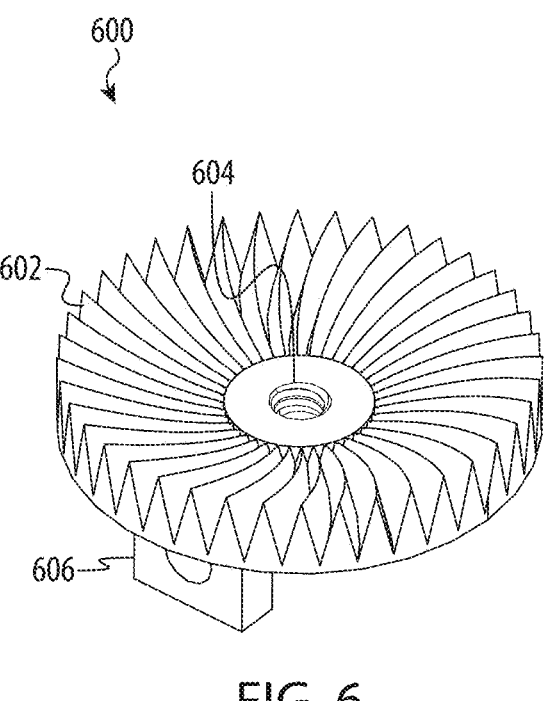
FIG. 6 shows an example rotational component for a prosthetic device.

FIG. 6 shows an example of a rotational component 600 for a prosthetic device, which can be an example of the rotational components described herein such as rotational component 322. The rotational component 600 can include a set of teeth 602 that can engage with the second component as described herein. In some cases, the teeth 602 can have a curved tooth structure such as shown in FIG. 6. In other cases, the teeth 602 can have a straight/radial structure, or any other suitable configuration. In some cases, the teeth 602 can be configured to promote defined movements, such as promoting movement in one direction and inhibiting or preventing movement in the other direction. For example, radially curved teeth 602 can be configured to facilitate movement in a first direction and inhibit movement in a second direction. In other embodiments the rotational component 600 can have other structures that are configured to engage with the second component to secure the second component in a specific axial orientation, as described herein.

The rotational component 600 can include a first coupling feature 604 that is used to attach the second component to the rotational component 600. The coupling feature 604 can be a threaded hole, or can couple to the rotational component 600 using other fastening techniques such as an interference fit, adhesive coupling, welding, or the like. The rotational component 600 can also include one or more posts 606 that are used to couple the rotational component to the first component, such as the first component/slider described herein. For example, the post(s) 606 can slide into the first component/slider and a bolt, screw, rod, pin, or other suitable structure can extend through a hole in the post(s) to secure the post to the first component.

Figure 7A:
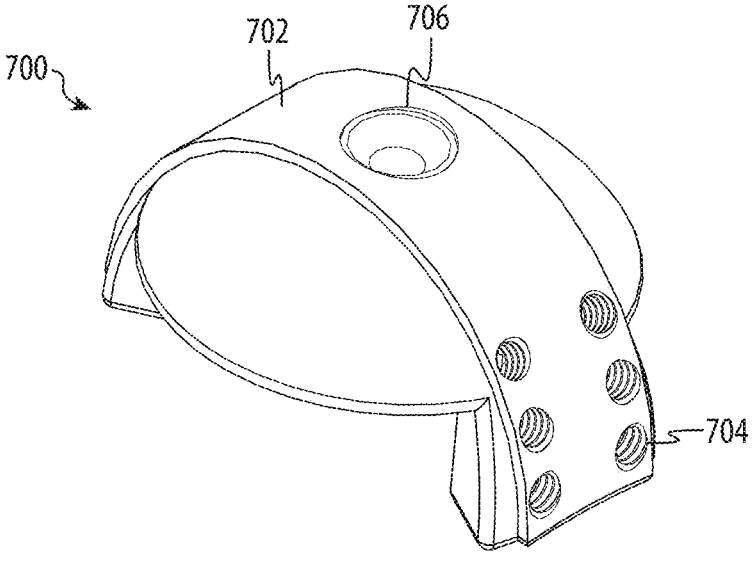
FIGS. 7A and 7B show an example second component for a prosthetic device.

FIG. 7A shows a top view of an example second component 700, which can be an example of the second component 308. The second component 700 may form a top portion of the carriage and attach a prosthetic digit to the carriage. The second component 700 can include an upper surface 702 that interfaces with the prosthetic digit. In some cases, the upper surface 702 can be formed to have a structure/shape that corresponds to the structure/shape of a mating surface of the prosthetic digit. For example, if a mating surface of the prosthetic thumb has a specific curvature, the upper surface 702 can have substantially the same curvature such that the two surfaces contact in a coincident relationship. The second component 700 can also include a dome portion which forms an outer surface of the second component 700 such as one or more surfaces surrounding the upper surface 702. In some cases, the upper surface 702 can also define the dome portion.

The second component 700 can also include one or more fastening features 704, one of which is labeled for clarity.

The fastening feature 704 can be used to attach a prosthetic digit to the second component 700. In some cases, the fastening features 704 can include a set of threaded holes that can be used to bolt the prosthetic digit to the second component 700. In other cases, the fastening features 704 can include snap connections, rivets, interference connections, or any other suitable fastening mechanism. In some embodiments, multiple fastening features 704 can allow a prosthetic digit to be positioned in different orientations relative to the second component 700.

The second component 700 can also include a top fastening feature 706 that can be used to attach the second component to the rotational component and/or the first component. In some embodiments, the top fastening feature 706 comprises a hole and a bolt that can be used to secure the second component 700 to the intermediate component and/or the first component.

Figure 7B:
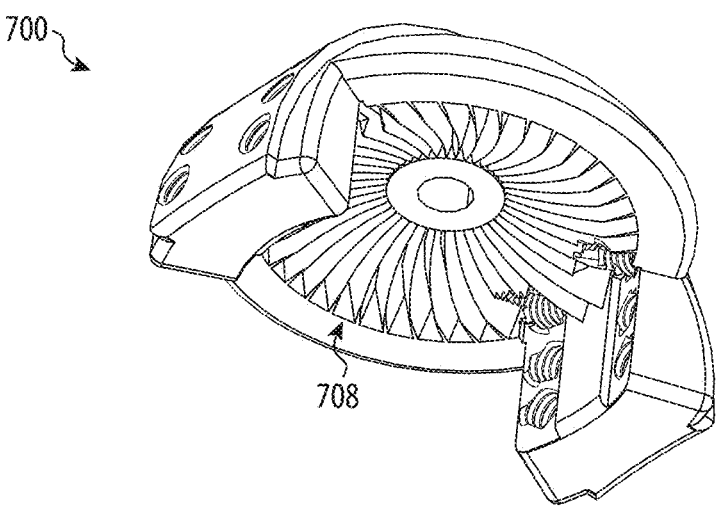

FIG. 7B shows a bottom view of the second component 700. The underside of the second component 700 can include a second set of teeth 708 that interfaces with the first set of teeth on the rotational component (e.g., 602 shown in FIG. 6), such as rotational component 600. In some cases, the second set of teeth 708 can have a curved tooth structure such as shown in FIG. 7. In other cases, the second set of teeth 708 can have a straight/radial structure, or any other suitable configuration.

Figures 8, 9:
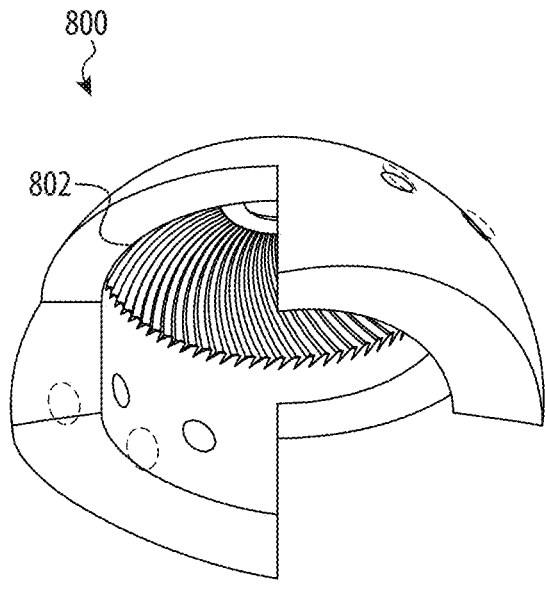
FIG. 8 shows an example second component for a prosthetic device.
FIG. 9 shows an example rotational component for a prosthetic device.

FIG. 8 shows another example second component 800 that includes a dome geared structure 802, while FIG. 9 shows another example rotational component 900 with a complementary dome geared structure 902 that engages with the dome geared structure 802 on the second component 800. The dome structure shown in FIGS. 8 and 9 can increase a contact area between the second component 800 and the rotational component 900 when assembled, which can increase the ability of the second component 800 and the rotational component 900 to resist rotation when locked together. The second component 800 can also include one or more fastening features 804 which can be used to attach a prosthetic digit to the second component 800. The rotational component 900 can be attached to a carriage using one or more fastening features 904, an example of which can include a thru hole for using a threaded fastener.

Figure 10A:
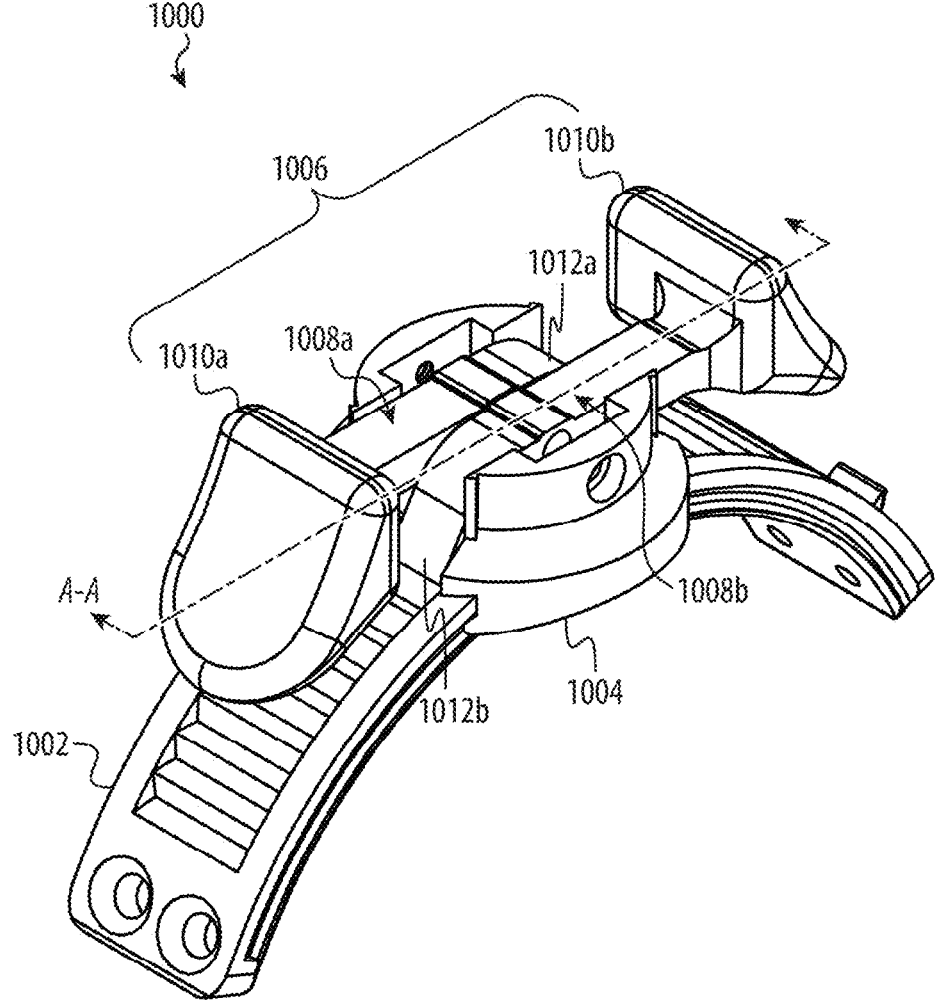
FIG. 10A shows an example locking mechanism for a prosthetic device.

FIG. 10A shows an example prosthetic device 1000 with the second component removed to show an example locking mechanism 1006. The prosthetic device 1000 can include a track 1002, which can be an example of the tracks described herein such as tracks 104, 302, and 400; a first component 1004 (e.g., slider), which can be an example of the first components described herein such as first components 306 and 500; and a locking mechanism 1006, which can be an example of the locking mechanism described herein such as locking mechanism 310.

The locking mechanism 1006 can include one or more locking members 1008, which can each include an actuator portion 1010 and a track engagement portion 1012. The locking mechanism 1006 can couple to the first component 1004 via a bolt, pin, or other suitable fastening mechanism as described herein. In some cases, the locking member(s) 1008 can be a lever with the actuator portion located at an opposite end of the locking member 1008 from the track engagement portion 1012. The actuator portion(s) 1010 can be configured to facilitate a user interaction with the locking mechanism 1006. For example, the actuator 1010a and/or 1010b can include a surface that has a surface area that is similar to a human finger.

Figure 10B:
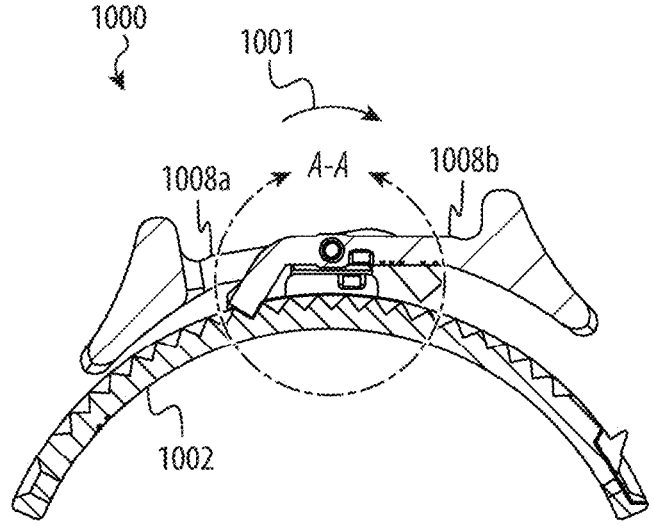
FIG. 10B shows a cross-sectional view of the example locking mechanism shown in FIG. 10A.
Figure 10C:
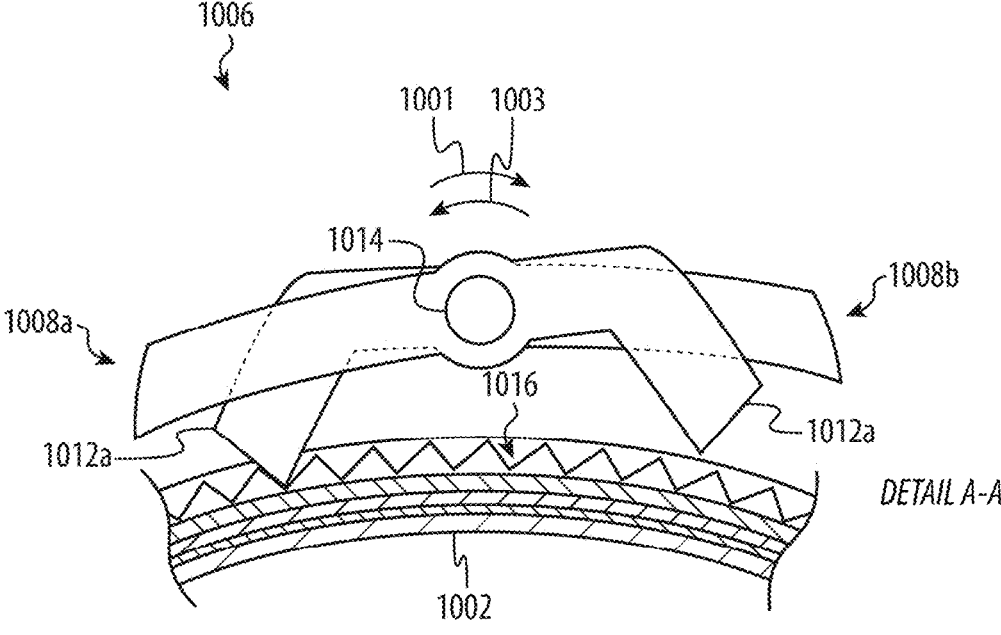
FIG. 10C shows a detail view of area A-A shown in FIG. 10B.

FIG. 10B shows a cross-sectional view of the prosthetic device 1000 taken along section A-A shown in FIG. 10A, and FIG. 10C shows a simplified detail view of the interaction of the locking mechanism 1006 with the track 1002, with certain elements removed for clarity. As shown in FIGS. 10B and 10C, the first locking member 1008a is depressed, which rotates the first locking member 1008a about the fastening feature 1014, which can be an example of the fastening features described herein such as fastening feature 316. This rotation causes the first track engagement portion 1012a to disengage from a locking feature 1016, thereby allowing the first component 1004 to slide along the track 1002 in the first direction 1001.

In some embodiments, the locking mechanism 1006 includes a single locking member 1008. The single locking member 1008 can be configured to prevent the first component 1004 (and carriage) from moving in a single direction when locked. For example, the track engagement portion 1012a can engage with locking features on the track 1002 to prevent movement in the first direction 1001, but allow movement in a second direction 1003. In some examples, as illustrated in FIGS. 10B and 10C, a directional ratcheting mechanism can be used to prevent the carriage 1004 from moving in a first direction without engaging the locking mechanism. In these cases, even when the locking member 1008 is engaged, the first component 1004 can move freely in the other direction along the track. In other embodiments with a single locking member 1008, the locking member 1008 can be configured to prevent movement in both directions along the track 1002. For example, the track engagement portion 1012 and locking features on the track 1002 can be configured to engage in a manner that prevents movement in either direction such as by having the track engagement portion 1012 engage with teeth on the track to prevent movement in either direction. Accordingly, in these cases, when the locking member is engaged with the track 1002, it can prevent movement of the first component 1004 in both directions along the track 1002.

In the embodiment shown in FIGS. 10A-10C, the locking mechanism can include a first locking member 1008a and a second locking member 1008b. The first locking member prevents movement of the first component 1004 along the first direction 1001, and the second locking member prevents movement of the first component 1004 along a second direction 1003.

The locking mechanism 1006 can also include bias elements 1018 that can cause one or more of the locking members 1008 to default to a locked or unlocked state. For example, a first biasing element 1018a can be positioned between the first component 1004 and the first member locking member 1008a. In this regard, the first biasing element 1018a can push upward on the first locking member 1008a to pivot it about the fastening feature 1014 thereby causing the first track engagement portion 1012a to engage with the track when the first locking member 1008a is not being actuated by the user. Accordingly, positioning the first biasing element 1018a on the opposite side of the fastening feature 1014 from the first track engagement portion 1012a portion can cause the first locking member 1008a to default to a locked state. Similar positioning of a second biasing element 1018b with respect to the second locking member 1008b can cause the second locking member 1008b to default to a locked state. In other cases, positioning the biasing elements 1018 to be on the same side of the fastening feature 1014 as the track engagement portion 1012 can cause the locking members to default to an unlocked state. In other examples, the biasing elements 1018 can be positioned above the locking members 1008 and push down on the locking members 1008 to cause them to engage with the track 1002. In FIG. 10C, the biasing members are both shown as not contacting the track 1002 or the locking mechanism for clarity. However, in the operation as illustrated in FIG. 10C, the first biasing element 1018*a* would be expanded and holding the first locking member 1008*a* in an upward position, and the second biasing element 1018*b* would be compressed by the second locking member 1008*b*.

In some embodiments, the locking mechanism 1006 may be configured to remain in its current state. For example, if a user actuates one of the locking members 1008 to a locked state, that locking member will remain in the locked state until actuated to an unlocked state. Similarly, if a user actuates one of the locking members 1008 to an unlocked state, that locking member will remain in the locked state until actuated to an unlocked state. In some cases, the locking mechanism 1006 can operate in such a manner by removing the biasing elements 1018. In this regard, frictional forces between the locking members 1008 and the first component 1004 can cause the locking members to remain in a given state. In other cases, the locking members 1008, the first component 1004, and/or the fastening feature 1014 can include mechanism(s) for retaining the locking members 1008 in an actuated state. These can include surface features such as protrusions and indentations on the different components that cause a "soft-lock" type feature.

Figure 11B:
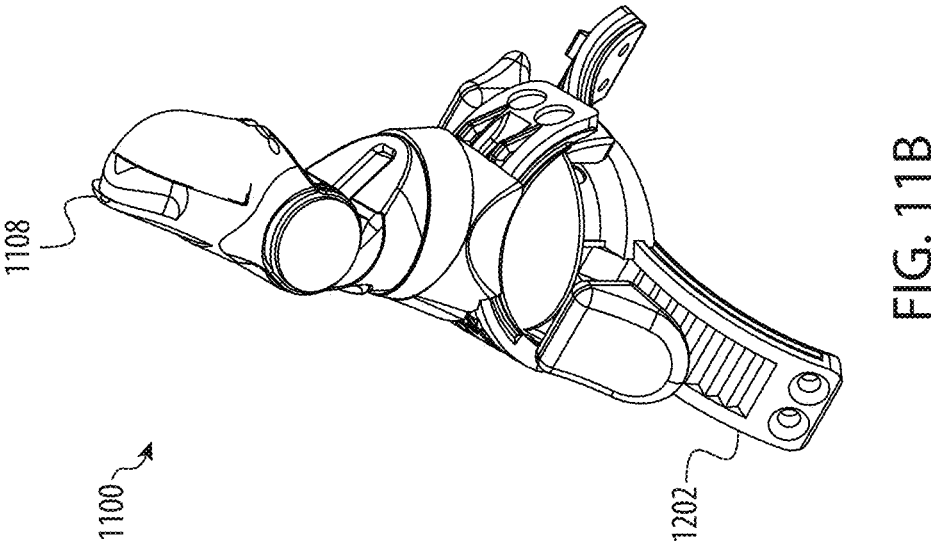
FIG. 11B show an example of the prosthetic device of FIG. 11A in a second axial position.
Figure 11A:
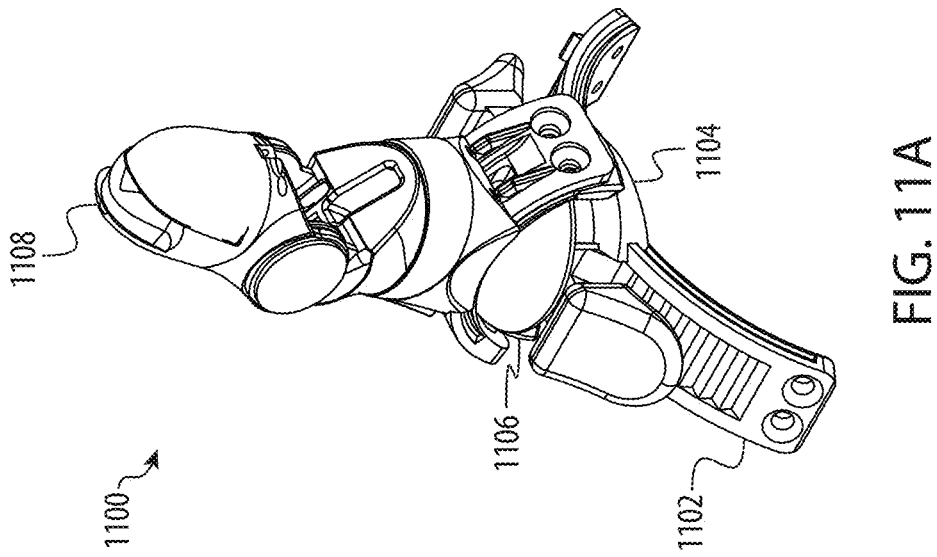
FIG. 11A shows an example of a prosthetic device in a first axial position.

FIGS. 11A and 11B show an example of rotational movement of a prosthetic device 1100. The prosthetic device 1100 can be an example of the prosthetic devices described herein such as prosthetic devices 100, 300, and 1000. The prosthetic device can include a rotational component (not shown) that allows the second component 1106 and the prosthetic digit 1108 to be axially rotated with respect to the first component 1104 and track 1102. FIG. 11A shows a first axial position of the prosthetic digit 1108 and FIG. 11B shows a second axial position of the prosthetic digit 1108. The first axial position of the prosthetic digit 1108 shown in FIG. 11A can result from a first set of teeth of the rotational component (e.g., 602 shown in FIG. 6) engaging in a first orientation with the second set of teeth (e.g., 708 shown in FIG. 7B). The second axial position of the prosthetic digit 1108 shown in FIG. 11B can result from a first set of teeth of the rotational member (e.g., 602 shown in FIG. 6) engaging in a second orientation with the second set of teeth (e.g., 708 shown in FIG. 7B).

Figure 12:
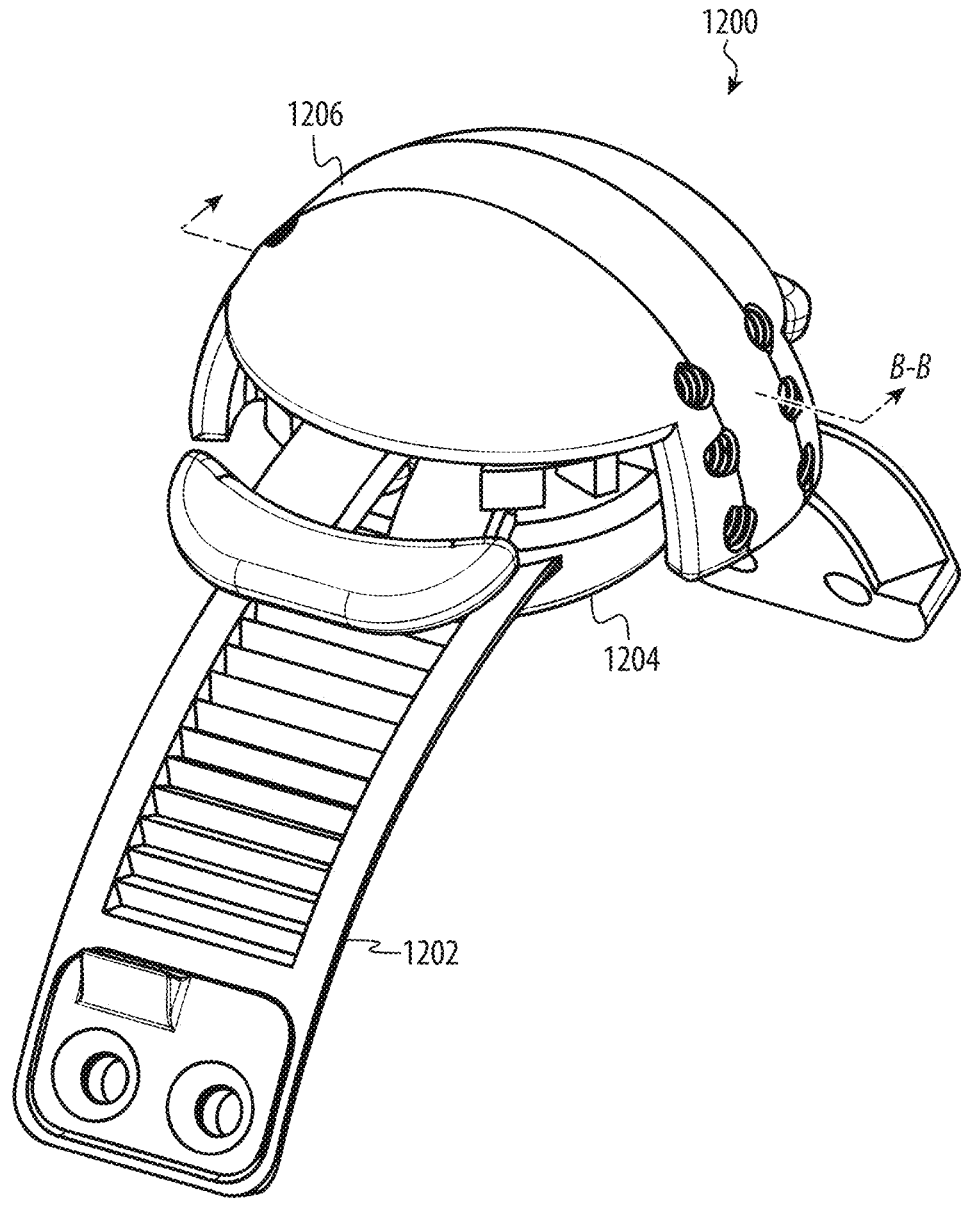
FIG. 12 shows an example prosthetic device including a rotating mechanism.

FIG. 12 shows an example prosthetic device 1200 that includes a second component 1206 that can be rotated by a user while a prosthetic digit is coupled to the prosthetic device 1200 and the prosthetic device is attached to a user. The prosthetic device 1200 can be an example of the prosthetic devices described herein such as prosthetic devices 100, 300, 1000, and 1100. The prosthetic device 1200 can allow a user to rotate a prosthetic digit with respect to a first component 1204 and a track 1202, for example as shown in FIGS. 11A and 11B.

The prosthetic device 1200 can include a rotating mechanism that includes the first component 1204 and the second component 1206. In a first state, the first component 1204 may engage with the second component 1206 to prevent movement of these components with respect to each other, which may be referred to as a locked configuration. In the locked configuration, a prosthetic digit attached to the prosthetic device 1200 may be held in a fixed orientation with respect to the first component 1204 and the second component 1206, and be able to move along the track 1202 as described herein. In a second state, the first component 1204 may at least partially disengage with the second component 1206 to allow the second component 1206 to be moved with respect to the first component 1204, which may be referred to as an unlocked configuration. In the unlocked configuration, a user may rotate a prosthetic digit to a new orientation with respect to the track 1202 and the first component. After moving the prosthetic digit to a new orientation, the rotating mechanism may transition back to the locked state.

The rotating mechanism may be biased to the locked state, and in the absence of a user actuation, the second component 1206 is fixed with respect with the first component 1204. In some cases, a user may transition the rotating mechanism from the locked state to the unlocked state by moving the second component 1206 toward the first component 1204. For example, the user may manually grasp a prosthetic digit attached to the second component to push the second component 1206 to the first component 1204. The movement of the second component 1206 toward the first component 1204 can unlock the rotating mechanism and allow the second component 1206 (and prosthetic digit) to be rotated as described herein. In other cases, the rotating mechanism may be unlocked in different ways. For example, the rotating mechanism may include a button or other feature that is actuated by the user to put the rotating mechanism in an unlocked state. In other examples, a user may pull the second component 1206 away from the first component to unlock the rotating mechanism.

Figure 13A:
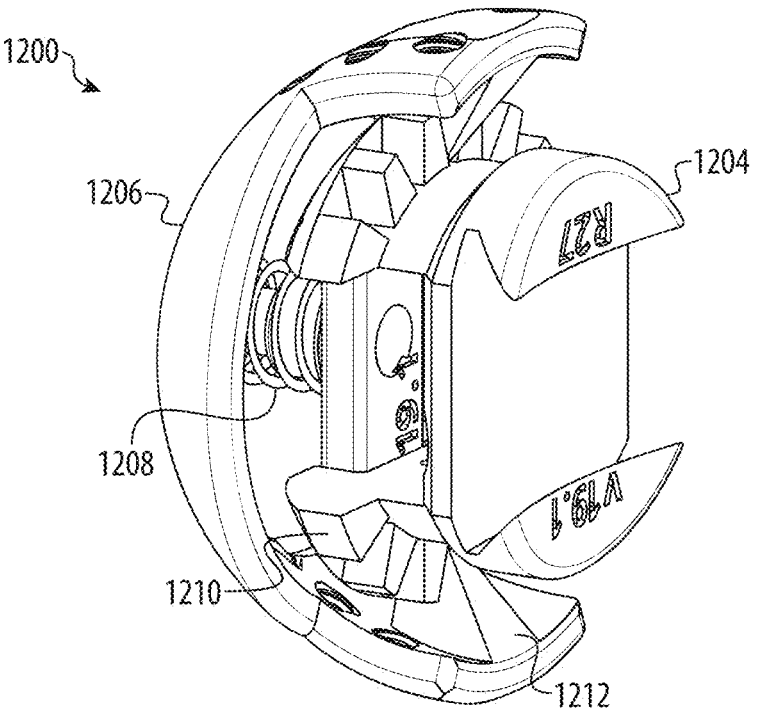
FIGS. 13A and 13B show an example operation of a rotating mechanism.
Figure 13B:
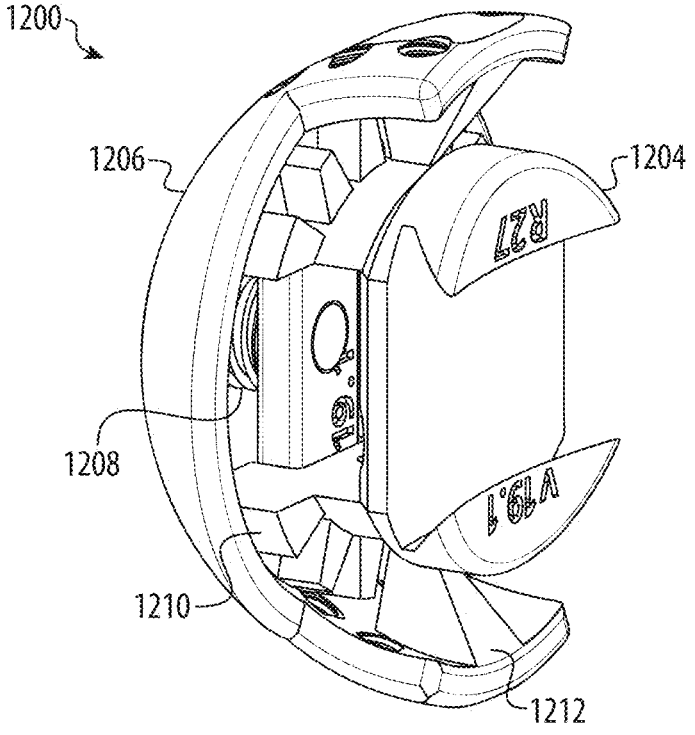

FIGS. 13A and 13B show an example operation of the rotating mechanism of the prosthetic device 1200. FIGS. 13A and 13B show bottom views of the rotating mechanism which can be a combination of components including the first component 1204, the second component 1206, and a biasing member 1208. The track 1202 has been removed from FIGS. 13A and 13B to show the components of the rotating mechanism. FIG. 13A shows an example of the rotating mechanism in a locked state and FIG. 13B shows an example of the rotating mechanism in an unlocked state.

The first component 1204 can include one or more retention features 1210 (one of which is labeled for clarity) and the second component 1206 can include one or more engagement features 1212 (one of which is labeled for clarity). The biasing element 1208 can include a spring or other feature that creates a biasing force to the locked state. For example, the retention features 1210 can be one or more sets of teeth, and in the locked state the engagement feature 1212 can be positioned between the teeth, which prevents rotational movement of the second component 1206 with respect to the first component 1204. In this state, the biasing element 1208 may provide a force that biases and holds the engagement features 1212 between the teeth of the retention features 1210. For example, the biasing element 1208 may provide a force that pushes the first component 1204 and the second component 1206 in opposite directions.

As shown in FIG. 13B, a user can transition the rotating mechanism to an unlocked state by moving the second component 1206 towards the first component 1204 and compressing the biasing element 1208. In this unlocked state, the engagement features 1206 are disengaged from the retention features 1210, which allows the second component 1206 to be rotated with respect to the first component 1204. In response to the removing a force (e.g., user force) that is compressing the biasing element 1208, the biasing element 1208 may move the second component 1206 such that the engagement features 1212 are positioned between the retention features 1210 thereby locking the rotating mechanism.

Figure 14:
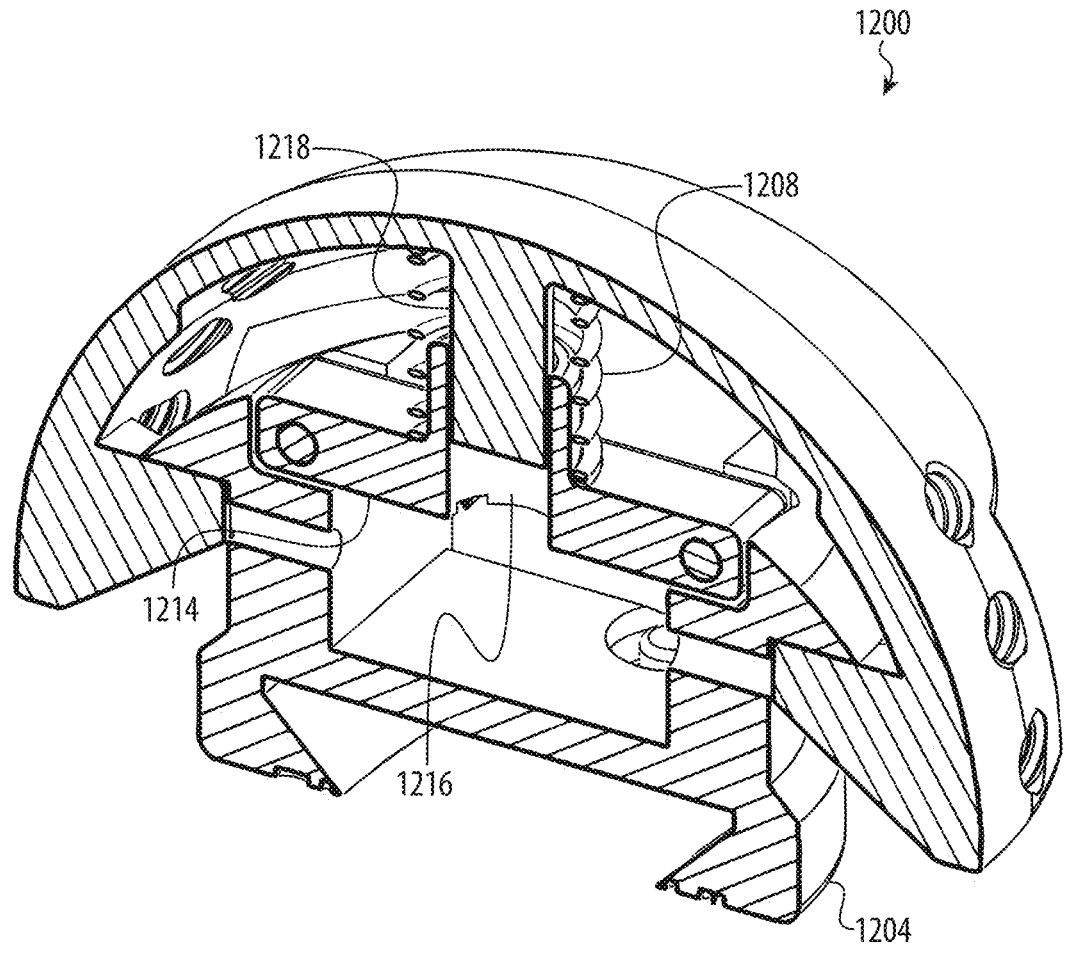
FIG. 14 shows a cross-sectional view of a prosthetic device shown in FIG. 12.

FIG. 14 shows a cross-sectional view of a prosthetic device 1200 taken along line B-B shown in FIG. 12. The rotating mechanism can be a combination of components including the first component 1204, the second component 1206, the biasing member 1208, and the support bracket 1214. In some cases, the support bracket 1214 can couple to the first component 1204. In other cases, the support bracket 1214 can be part of the first component 1204, for example, being a continuous piece of material with the first component. The support bracket 1214 can support the biasing element 1208. Additionally or alternatively, the support bracket 1214 can couple with the second component 1206 to control the direction of movement of the second component 1206. For example, the support bracket 1214 may define a sleeve 1216 and the second component may define a rod 1218 that fits in the sleeve. The sleeve 1216 and the rod 1218 may have a linear motion path between the second component 1206 and the first component 1204. Additionally, the sleeve 1216 and the rod 1218 may allow the second component 1206 to rotate with the first component, for example when the rotating mechanism is in an unlocked state as described herein.

In some cases, the support bracket 1214 can limit movement of the second component with respect to the first component 1204. For example, as the second component 1206 is moved downward and the biasing element 1208 is compressed, an inside surface of the support bracket 1214 may contact an upper portion of the support bracket (e.g., upper portion of the sleeve 1216) which may prevent further downward movement of the second component 1206 toward the first component.

Figure 15:
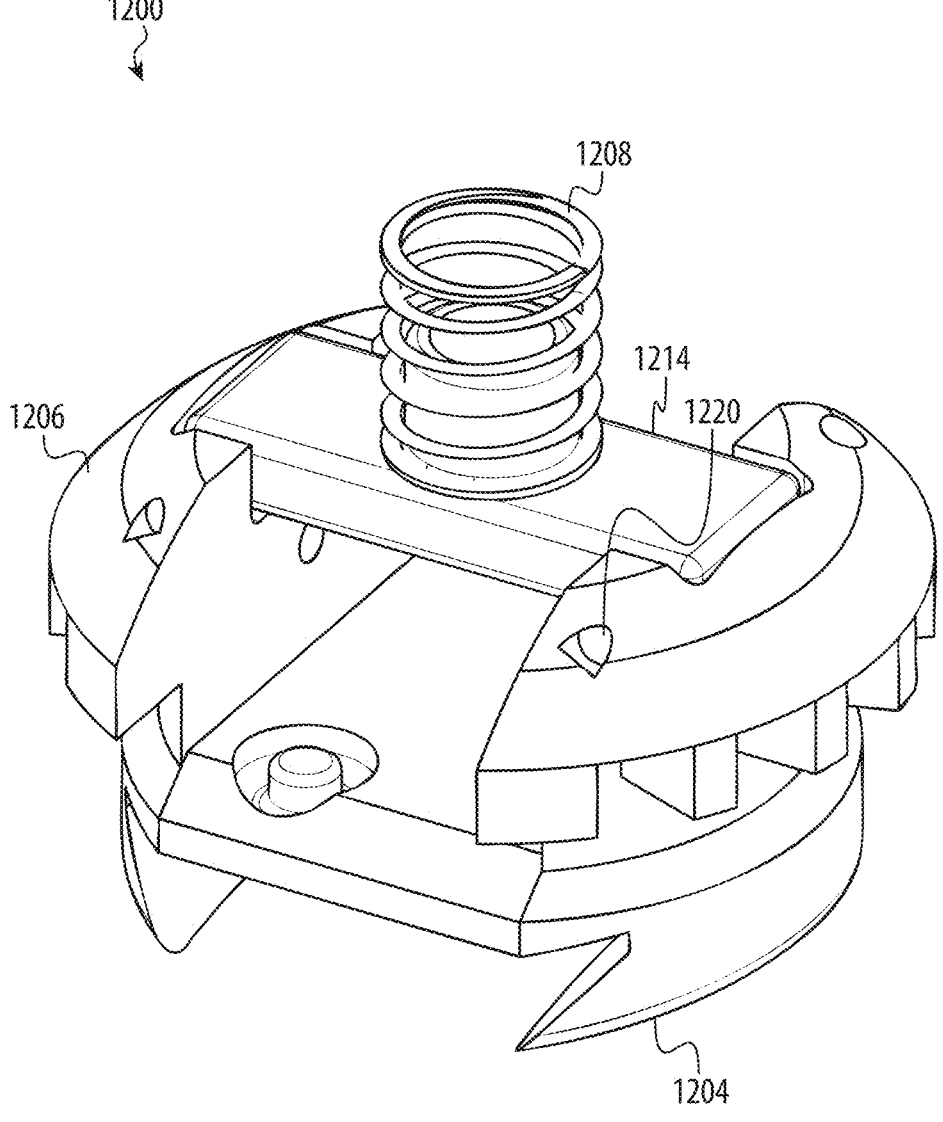
FIG. 15 shows an example sub assembly of the prosthetic device shown in FIG. 12.

FIG. 15 shows an example sub assembly of the prosthetic device 1200 shown in FIG. 12 and including the first component 1204, the second component 1206, the biasing element 1208, and the support bracket 1214. In cases where the support bracket 1214 is a separate component from the first component 1204, the support bracket 1214 can be rigidly coupled to the first component 1204 to fix the support bracket 1214 with respect to the first component 1204. This can include using a fastener 1220 such as a pin, rod, screw, or any other suitable fastener. In other cases, the support bracket 1214 can be adhesively coupled, press fit welded, brazed, or otherwise coupled to the first component 1204.

Figure 16:
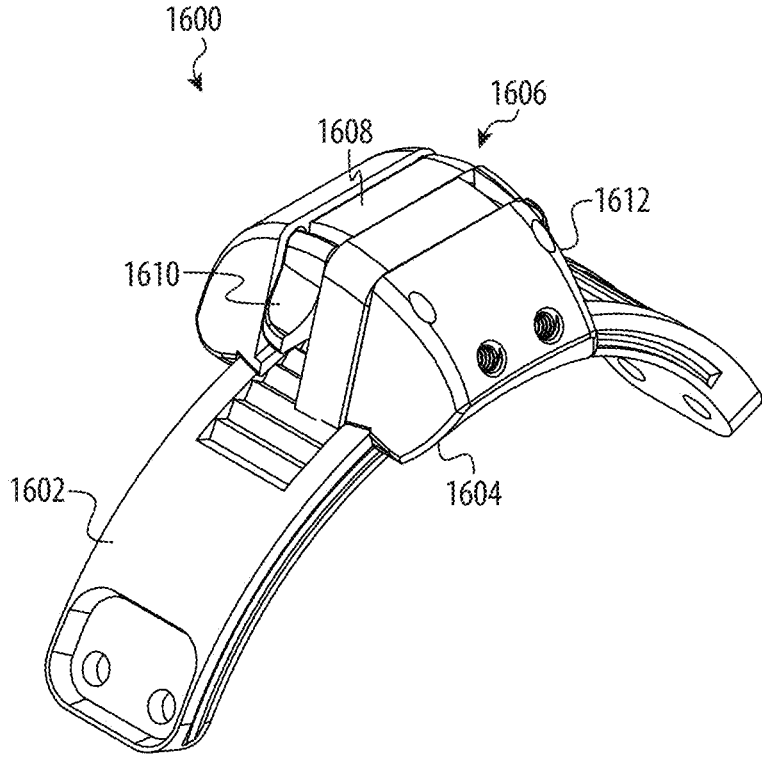
FIG. 16 shows an alternative example prosthetic device.

FIG. 16 shows an example prosthetic device 1600 with an alternative locking mechanism 1606. The prosthetic device 1600 can include a track 1602, which can be an example of the tracks described herein such as tracks 104, 302, and 400; and a carriage 1604, which may be an example of the carriages described herein such as carriages 106 and 304. The locking mechanism 1606 can include one or more locking members 1608, one of which is labeled for simplicity. When an actuator 1610 of the locking member 1608 is pressed, the locking member 1608 can pivot about pin 1612 to disengage the locking member from the track 1602. In this regard, locking mechanism 1606 can have a pivot axis (e.g., pin 1612) for each locking member 1608. In other embodiments, the pin 1612 can be implemented as a bolt, or any other suitable structure that allows the locking member to pivot with respect to the carriage 1604.

Figure 17:
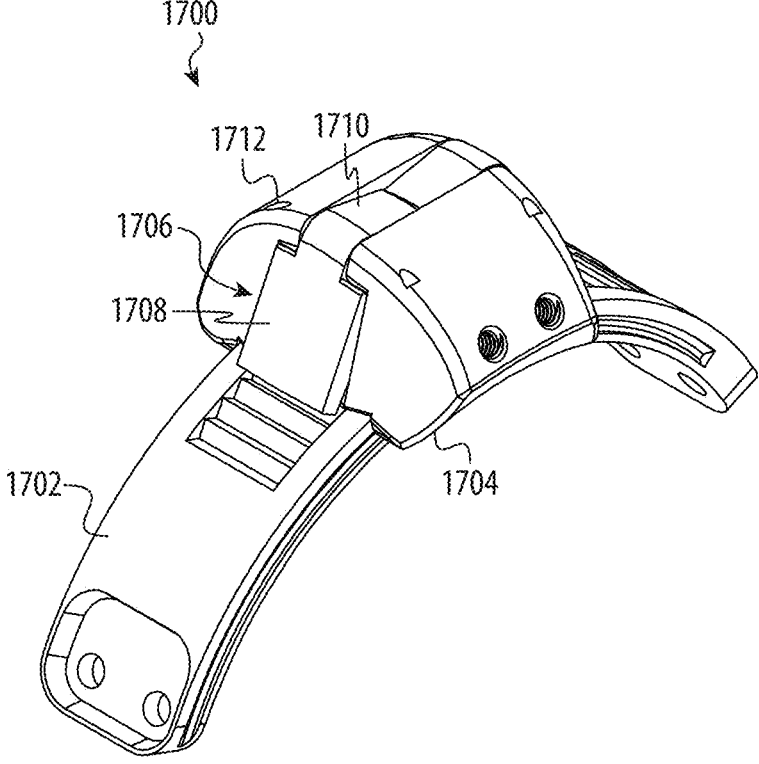
FIG. 17 shows another alternative example prosthetic device.

FIG. 17 shows an example prosthetic device 1700 with an alternative locking mechanism 1706. The prosthetic device 1700 can include a track 1702, which can be an example of the tracks described herein such as tracks 104, 302, and 400; and a carriage 1704, which may be an example of the carriages described herein such as carriages 106 and 304. The locking mechanism 1706 can include one or more locking members 1708 one of which is labeled for simplicity. When an actuator 1710 of the locking member 1708 is pressed, the locking member 1708 can pivot about pin 1712 to disengage the locking member from the track 1702. In this regard, locking mechanism 1706 can have a pivot axis (e.g., pin 1712) for each locking member 1708. In other embodiments, the pin 1712 can be implemented as a bolt, or any other suitable structure that allows the locking member to pivot with respect to the carriage 1704.

Figure 18:
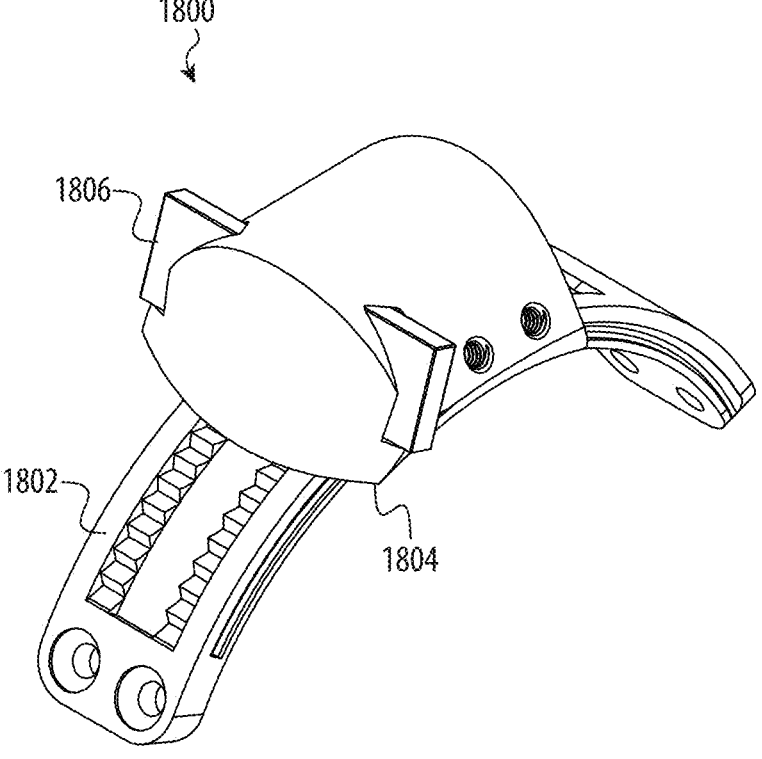
FIG. 18 shows another alternative example prosthetic device.

FIG. 18 shows an example prosthetic device 1800 with an alternative locking mechanism. The prosthetic device 1800 can include a track 1802, which can be an example of the tracks described herein such as tracks 104, 302, and 400; and a carriage 1804, which may be an example of the carriages described herein such as carriages 106 and 304. The locking mechanism can be implemented as a locking member 1806 that when pushed to a first location relative to the carriage 1804 causes the locking mechanism to disengage from the track 1802 to allow the carriage 1804 to move along the track 1802. When the locking member 1806 is pushed to a second location relative to the carriage 1804, the locking member 1806 engages with the track 1802 to prevent movement of the carriage 1804 along the track 1802. In some cases, the locking mechanism can independently control movement of the carriage 1804 in different directions. For example, a first location of the locking member 1806 allows the carriage 1804 to move in a first direction and prevents movement in a second direction; a second location of the locking member 1806 prevents movement in the first direction and allows movement in the second direction; a third location of the locking member 1806 allows movement in both directions; and a fourth position of the locking member 1806 can prevent movement in both directions.

Figure 19A:
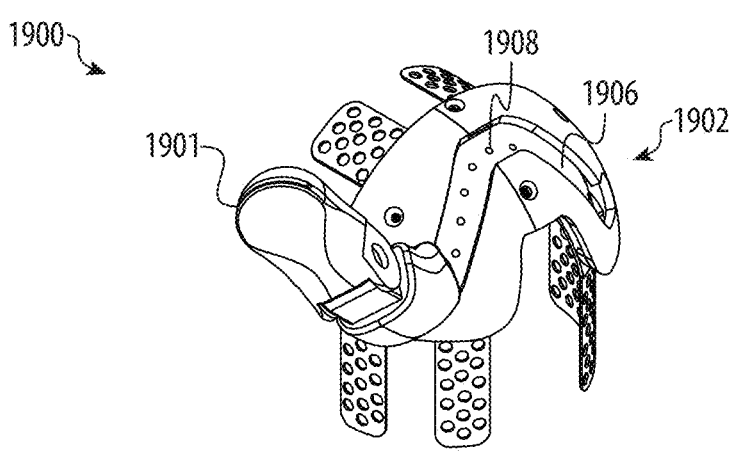
FIG. 19A shows another alternative example of a prosthetic device.
Figure 19B:
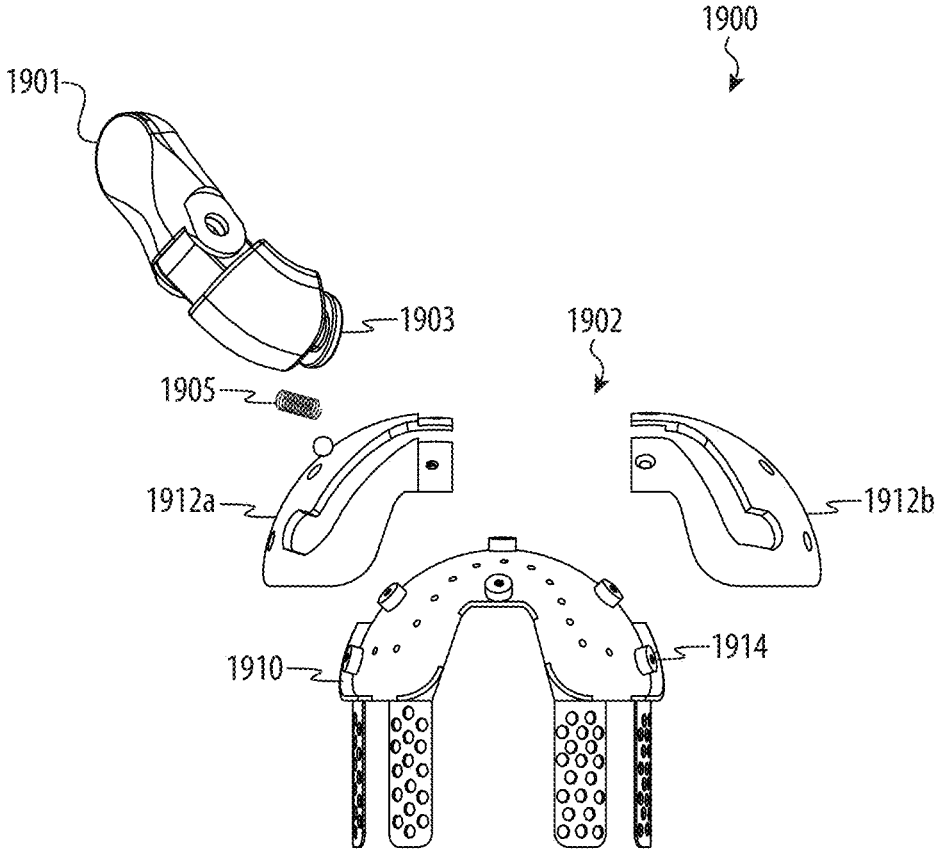
FIG. 19B shows an exploded view of the prosthetic device of FIG. 19A.

FIG. 19A shows an example of a prosthetic device 1900 and FIG. 19B shows an exploded view of the prosthetic device 1900. The prosthetic device 1900 can include a track plate 1902 that can be attached to a prosthetic socket to couple a prosthetic digit 1901, such as a thumb, to a user. The track plate 1902 can include a channel 1906 that attaches to the prosthetic digit 1901 and allows the prosthetic digit 1901 to move along the channel 1906 such that it can be positioned in different orientations relative to other fingers of the hand as described herein. One or more locking features 1908 can be positioned at different locations along the channel 1906 such that the prosthetic digit 1901 can be secured at different positions along the channel 1906.

As shown in FIG. 19B, the track plate 1902 can include a mounting interface 1910 and one or more channel plates 1912. The mounting interface 1910 can have a set of stand-off features 1914 (one of which is labeled for simplicity) that positions the channel plate(s) 1912 in an offset orientation. A sliding component 1903 can be mounted to a base of the prosthetic digit 1901, be at least partially positioned within the channel 1906 and captured between the mounting interface 1910 and the channel plates 1912. The sliding component 1903 can allow the prosthetic thumb to slide along the channel 1906. In some embodiments, the prosthetic device 1900 can include a biasing element 1905 such as a spring that is positioned between the sliding component and the mounting interface. The biasing element 1905 can engage with the locking feature(s) 1908 to secure the prosthetic digits in specific locations along the channel 1906. In some cases, the biasing component can include a ball-detent mechanism where a spring feature pushes a ball into the depressed locking feature 1908. This can create a "soft lock" that can be overcome by a user applying more force to dislodge the ball detent from the depressed locking feature 1908. Additionally or alternatively, the biasing element 1905 can help stabilize the prosthetic digit 1901 by pushing the sliding component against an underside of the channel plate(s) 1912.

During operation a user can move the prosthetic digit 1901 to a desired location along the channel that corresponds to one of the locking features. In some cases, the sliding component 1903 can be configured to control rotation of the prosthetic digit 1901 as it moves along the channel 1906. For example, the sliding component 1903 can have an elliptical profile and the channel plates 1912 can define a channel structure that causes the sliding component to rotate in a defined path as it traverses the channel 1906. Accordingly, the prosthetic device 1900 can be configured to orient the prosthetic digit 1901 in different angular orientations depending on its position to other digits of the hand, which may place the thumb in a more natural position to help a user perform specific functions such as gripping an object.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A device for mounting a prosthetic finger, the device comprising:
   a track configured to attach to a prosthetic socket;
   a carriage comprising:
      a first component coupled to the track;
      a second component comprising a partial dome structure, coupled to the first component and at least partially containing the first component, and configured to couple with the prosthetic finger, wherein:
         in a first state, the second component is rotationally fixed with respect to the first component; and
         in a second state, the second component is configured to rotate with respect to the first component; and
      a biasing element coupled to the first component and the second component and configured to bias the first component and the second component to the first state.

2. The device of claim 1, wherein:
   the first component comprises retention features;
   the second component comprises engagement features that are configured to engage with the retention features;
   in the first state, the engagement features and the retention features prevent the second component from rotating with respect to the first component; and
   in the second state, the engagement features and the retention features disengage to allow the second component to rotate with respect to the first component.

3. The device of claim 1, wherein:
   the biasing element is positioned between the first component and the second component; and
   movement of the first component toward the second component compresses the biasing element and transitions the carriage from the first state to the second state.

4. The device of claim 1, wherein the first component is configured to move along the track.

5. The device of claim 4, further comprising a locking mechanism coupled to the carriage and operable to transition between:
   a first state that prevents movement of the first component along the track in a first direction and a second direction opposite the first direction;
   a second state that allows the first component to move along the track in the first direction; and
   a third state that allows the first component to move along the track in the second direction.

6. The device of claim 5, wherein the locking mechanism comprises:
   a first lever positioned on a first side of the carriage; and
   a second lever positioned on a second side of the carriage.

7. The device of claim 6, wherein:
   in the first state, the first and second levers engage with the track to prevent movement of the first component along the track;
   in the second state, the first lever disengages with the track to allow the first component to move along the track in the first direction; and
   in the third state, the second lever disengages with the track to allow the first component to move along the track in the second direction.

8. The device of claim 6, wherein:
   the first state is a default state;
   in response to the first lever being depressed, the locking mechanism transitions from the first state to the second state; and
   in response to the first lever being released, the locking mechanism transitions from the second state to the first state.

9. The device of claim 8, wherein:
   in response to the second lever being depressed, the locking mechanism transitions from the first state to the third state; and
   in response to the second lever being released, the locking mechanism transitions from the third state to the first state.

10. A device for mounting a prosthetic finger to a socket, the device comprising:
    a track defining a curved profile;
    a first component coupled to the track;
    a second component coupled to the first component and is configured to couple with the prosthetic finger;
    a spring positioned between the first component and the second component, wherein:
       in an unlocked state, the second component is configured to rotate with respect to the first component;
       in a locked state, the second component is rotationally fixed with respect to the first component; and
       the spring is configured to bias the first component and the second component in the locked state.

11. The device of claim 10, wherein:
    the first component comprises retention features;
    the second component comprises engagement features; and
    in the locked state, the engagement features are configured to engage with the retention features in multiple different configurations, and each respective configuration of the multiple different configurations defines a different angular orientation between the first component and the second component.

12. The device of claim 11, wherein:
    the retention features comprise a first set of gear teeth; and
    the engagement features define a second set of gear teeth that engage with the first set of gear teeth.

13. The device of claim 10, wherein:

the second component is configured to move from an undepressed position with respect to the first component and to a depressed position with respect to the first component;

the locked state comprises the undepressed position; and the unlocked state comprises the depressed position.

14. The device of claim 13, wherein:

the spring is configured to maintain the second component in the undepressed position; and in response to an input force, the second component compresses the spring and moves to the depressed position.

15. The device of claim 10, wherein:

the second component comprises a partial dome structure; and the second component is configured to at least partially contain the first component.

16. A device for mounting a prosthetic finger, the device comprising:

a track configured to attach to a prosthetic socket;

a carriage configured to move along the track in a first direction or a second direction, opposite the first direction and comprising:

a first component coupled to the track and is operable to move along the track;

a second component coupled to the first component and is configured to couple with the prosthetic finger;

a biasing element coupled to the first component and the second component, wherein in an unlocked state, the second component is configured to rotate with respect to the first component, in a locked state, the second component is rotationally fixed with respect to the first component, and the biasing element is configured to bias the first component and the second component in the locked state; and a locking mechanism coupled to the carriage and operable to transition between a first state that prevents movement of the carriage along the track in the first direction and the second direction, a second state that allows the first component to move along the track in the first direction, and a third state that allows the first component to move along the track in the second direction.

17. The device of claim 16, wherein:

the locking mechanism comprises:

a first lever positioned on a first side of the carriage; and a second lever positioned on a second side of the carriage; and in the first state, the first and second levers engage with the track to prevent the movement of the first component along the track;

in the second state, the first lever disengages with the track to allow the first component to move along the track in the first direction; and in the third state, the second lever disengages with the track to allow the first component to move along the track in the second direction.

18. The device of claim 16, wherein the track comprises a curved profile extending from a first end to a second end.

\* \* \* \* \*